(12) United States Patent
Fuller et al.

(10) Patent No.: US 11,759,585 B2
(45) Date of Patent: Sep. 19, 2023

(54) NASAL DRUG DELIVERY DEVICE WITH DETACHABLE NOZZLE

(71) Applicant: Impel Pharmaceuticals Inc., Seattle, WA (US)

(72) Inventors: Christopher William Fuller, Seattle, WA (US); Craig Frederick Kohring, Seattle, WA (US); Albert Kenneth Lavin, Seattle, WA (US); John D. Hoekman, Seattle, WA (US)

(73) Assignee: Impel Pharmaceuticals Inc., Seattle, WA (US)

( * ) Notice: Subject to any disclaimer, the term of this patent is extended or adjusted under 35 U.S.C. 154(b) by 187 days.

(21) Appl. No.: 17/420,640

(22) PCT Filed: Dec. 17, 2019

(86) PCT No.: PCT/US2019/066921
§ 371 (c)(1),
(2) Date: Jul. 2, 2021

(87) PCT Pub. No.: WO2020/142206
PCT Pub. Date: Jul. 9, 2020

(65) Prior Publication Data
US 2022/0088327 A1 Mar. 24, 2022

Related U.S. Application Data

(60) Provisional application No. 62/788,093, filed on Jan. 3, 2019.

(51) Int. Cl.
*A61M 15/08* (2006.01)
*A61M 15/00* (2006.01)
*A61M 11/02* (2006.01)

(52) U.S. Cl.
CPC ............ *A61M 15/08* (2013.01); *A61M 11/02* (2013.01); *A61M 15/007* (2014.02); *A61M 15/009* (2013.01)

(58) Field of Classification Search
CPC .... A61M 15/08; A61M 15/009; A61M 11/02; A61M 2039/1016; A61M 2039/1027; F16L 37/0982; F16L 37/0985
See application file for complete search history.

(56) References Cited

U.S. PATENT DOCUMENTS 2,263,293 A  *  11/1941  Ewald ..................... F16L 37/40
                                                                251/149.6
2,420,866 A  *   5/1947  Coss ....................... A47L 9/242
                                                                285/317
(Continued)

FOREIGN PATENT DOCUMENTS

CL       199600872       12/1997
CL       200601054       12/2006
(Continued)

OTHER PUBLICATIONS

Appasaheb, et al., "Review on Intranasal Drug Delivery System", Journal of Advanced Pharmacy Education and Research, vol. 3, Issue 4, Oct. 2013, 14 pages.
(Continued)

*Primary Examiner* — Kathryn E Ditmer
(74) *Attorney, Agent, or Firm* — Fenwick & West LLP

(57) ABSTRACT

A nasal drug delivery device for delivering a plume derived from a propellant and a drug compound. The drug compound is in an intranasal dosage form in the form of powder, suspension, dispersion, or liquid. The propelled intranasal dosage form is deposited within the upper nasal cavity such as the olfactory region. The drug deposited within the olfactory region is delivered to the brain avoiding the blood-brain-barrier. Hydrofluoroalkane propellant from a
(Continued)

pressurized canister is channeled to a diffuser and drug-containing channel where the intranasal dosage form is aerosolized. The aerosolized intranasal dosage form passes through a nozzle thus delivering a plume to the user's upper nasal cavity.

25 Claims, 12 Drawing Sheets

(56) References Cited

U.S. PATENT DOCUMENTS

| | | | |
|---|---|---|---|
| 2,582,446 A * | 1/1952 | Martinet | A47L 9/242 |
| | | | 285/317 |
| 2,933,259 A | 4/1960 | Raskin | |
| 3,425,414 A | 2/1969 | Roche | |
| 3,888,253 A | 6/1975 | Watt et al. | |
| 3,906,950 A | 9/1975 | Cocozza | |
| 3,908,654 A | 9/1975 | Lhoest et al. | |
| 3,971,377 A | 7/1976 | Damani | |
| 4,095,596 A | 6/1978 | Grayson | |
| 4,151,750 A | 5/1979 | Suovaniemi et al. | |
| 4,187,985 A | 2/1980 | Goth | |
| 4,227,522 A | 10/1980 | Carris | |
| 4,353,365 A | 10/1982 | Hallworth et al. | |
| 4,412,573 A | 11/1983 | Zdeb | |
| 4,620,670 A | 11/1986 | Hughes | |
| 4,702,415 A | 10/1987 | Hughes | |
| 4,758,023 A * | 7/1988 | Vermillion | F16L 11/111 |
| | | | 285/903 |
| 4,896,832 A | 1/1990 | Howlett | |
| 4,995,385 A | 2/1991 | Valentini et al. | |
| 5,064,122 A | 11/1991 | Kamishita et al. | |
| 5,224,471 A | 7/1993 | Marelli et al. | |
| 5,307,953 A | 5/1994 | Regan | |
| 5,331,954 A | 7/1994 | Rex et al. | |
| 5,349,947 A | 9/1994 | Newhouse et al. | |
| 5,366,122 A * | 11/1994 | Guentert | A61M 13/00 |
| | | | 128/200.22 |
| 5,382,236 A | 1/1995 | Otto et al. | |
| 5,398,850 A | 3/1995 | Sancoff et al. | |
| 5,435,282 A | 7/1995 | Haber et al. | |
| 5,447,343 A * | 9/1995 | Gajewski | A61B 1/00128 |
| | | | 285/308 |
| 5,505,193 A | 4/1996 | Ballini et al. | |
| 5,516,006 A | 5/1996 | Meshberg | |
| 5,702,362 A | 12/1997 | Herold et al. | |
| 5,711,488 A | 1/1998 | Lund | |
| 5,715,811 A | 2/1998 | Ohki et al. | |
| 5,722,698 A * | 3/1998 | Amoretti | F16L 39/005 |
| | | | 285/317 |
| 5,797,390 A | 8/1998 | McSoley | |
| 5,814,020 A | 9/1998 | Gross | |
| 5,819,730 A | 10/1998 | Stone et al. | |
| 5,823,183 A | 10/1998 | Casper et al. | |
| 5,881,719 A | 3/1999 | Gottenauer et al. | |
| 5,901,703 A | 5/1999 | Ohki et al. | |
| 5,906,198 A | 5/1999 | Flickinger | |
| 5,910,301 A | 6/1999 | Farr et al. | |
| 5,954,696 A | 9/1999 | Ryan | |
| 6,062,213 A | 5/2000 | Fuisz et al. | |
| 6,092,522 A | 7/2000 | Calvert et al. | |
| 6,145,703 A | 11/2000 | Opperman | |
| 6,158,676 A | 12/2000 | Hughes | |
| 6,180,603 B1 | 1/2001 | Frey | |
| 6,186,141 B1 | 2/2001 | Pike et al. | |
| 6,189,739 B1 | 2/2001 | von Schuckmann | |
| 6,294,153 B1 | 9/2001 | Modi | |
| 6,302,101 B1 | 10/2001 | Py | |
| 6,313,093 B1 | 11/2001 | Frey | |
| 6,347,789 B1 | 2/2002 | Rock | |
| 6,367,471 B1 | 4/2002 | Genosar et al. | |
| 6,367,473 B1 | 4/2002 | Kafer | |
| 6,382,465 B1 | 5/2002 | Greiner Perth | |
| 6,410,046 B1 | 6/2002 | Lerner | |
| 6,491,940 B1 | 12/2002 | Levin | |
| 6,540,983 B1 | 4/2003 | Adjei et al. | |
| 6,569,463 B2 | 5/2003 | Patel et al. | |
| 6,585,172 B2 | 7/2003 | Arghyris | |
| 6,585,957 B1 | 7/2003 | Adjei et al. | |
| 6,585,958 B1 | 7/2003 | Keller et al. | |
| 6,595,202 B2 | 7/2003 | Gañán-Calvo | |
| 6,622,721 B2 | 9/2003 | Vedrine et al. | |
| 6,644,305 B2 | 11/2003 | MacRae et al. | |
| 6,644,309 B2 | 11/2003 | Casper et al. | |
| 6,647,980 B1 | 11/2003 | Gizurarson | |
| 6,681,767 B1 | 1/2004 | Patton et al. | |
| 6,684,879 B1 | 2/2004 | Coffee et al. | |
| 6,701,916 B2 | 3/2004 | Mezzoli | |
| 6,715,485 B1 | 4/2004 | Djupesland | |
| 6,734,162 B2 | 5/2004 | Van Antwerp et al. | |
| 6,810,872 B1 | 11/2004 | Ohki et al. | |
| 6,923,988 B2 | 8/2005 | Patel et al. | |
| 6,991,785 B2 | 1/2006 | Frey, II | |
| 7,033,598 B2 | 4/2006 | Lerner | |
| 7,051,734 B2 | 5/2006 | Casper et al. | |
| 7,163,013 B2 | 1/2007 | Harrison | |
| 7,182,277 B2 | 2/2007 | Vedrine et al. | |
| 7,200,432 B2 | 4/2007 | Lerner et al. | |
| 7,214,209 B2 | 5/2007 | Mazzoni | |
| 7,231,919 B2 | 6/2007 | Giroux | |
| 7,258,119 B2 | 8/2007 | Mazzoni | |
| 7,296,566 B2 * | 11/2007 | Alchas | A61M 15/0025 |
| | | | 128/200.22 |
| 7,347,201 B2 | 3/2008 | Djupesland | |
| 7,377,901 B2 | 5/2008 | Djupesland et al. | |
| 7,476,689 B2 | 1/2009 | Santus et al. | |
| 7,481,218 B2 | 1/2009 | Djupesland | |
| 7,543,581 B2 | 6/2009 | Djupesland | |
| 7,655,619 B2 | 2/2010 | During et al. | |
| 7,740,014 B2 | 6/2010 | Djupesland | |
| 7,784,460 B2 | 8/2010 | Djupesland et al. | |
| 7,799,337 B2 | 9/2010 | Levin | |
| 7,832,394 B2 | 11/2010 | Schechter et al. | |
| 7,841,337 B2 | 11/2010 | Djupesland | |
| 7,841,338 B2 | 11/2010 | Dunne et al. | |
| 7,854,227 B2 | 12/2010 | Djupesland | |
| 7,866,316 B2 | 1/2011 | Giroux | |
| 7,905,229 B2 | 3/2011 | Giroux et al. | |
| 7,934,503 B2 | 5/2011 | Djupesland et al. | |
| 7,975,690 B2 | 7/2011 | Djupesland | |
| 7,994,197 B2 | 8/2011 | Cook et al. | |
| 8,001,963 B2 | 8/2011 | Giroux | |
| 8,047,202 B2 | 11/2011 | Djupesland | |
| 8,119,639 B2 | 2/2012 | Cook et al. | |
| 8,122,881 B2 | 2/2012 | Giroux | |
| 8,146,589 B2 | 4/2012 | Djupesland | |
| 8,171,929 B2 | 5/2012 | Djupesland et al. | |
| 8,181,591 B1 * | 5/2012 | Gulka | A61M 15/009 |
| | | | 128/200.14 |
| 8,327,844 B2 | 12/2012 | Djupesland | |
| 8,408,427 B2 | 4/2013 | Wong | |
| 8,448,637 B2 | 5/2013 | Giroux | |
| 8,511,303 B2 | 8/2013 | Djupesland | |
| 8,517,026 B2 | 8/2013 | Amon | |
| 8,522,778 B2 | 9/2013 | Djupesland | |
| 8,550,073 B2 | 10/2013 | Djupesland | |
| 8,555,877 B2 | 10/2013 | Djupesland | |
| 8,555,878 B2 | 10/2013 | Djupesland | |
| 8,596,278 B2 | 12/2013 | Djupesland | |
| 8,733,342 B2 | 5/2014 | Giroux et al. | |
| 8,757,146 B2 | 6/2014 | Hoekman et al. | |
| 8,800,555 B2 | 8/2014 | Djupesland | |
| 8,839,790 B2 | 9/2014 | Amon | |
| 8,875,794 B2 | 11/2014 | Carlsen et al. | |
| 8,899,229 B2 | 12/2014 | Djupesland et al. | |
| 8,899,230 B2 | 12/2014 | Immel | |
| 8,910,629 B2 | 12/2014 | Djupesland et al. | |
| 8,925,544 B2 | 1/2015 | Flickinger | |
| 8,978,647 B2 | 3/2015 | Djupesland et al. | |
| 8,987,199 B2 | 3/2015 | Abdel Maksoud et al. | |
| 9,010,325 B2 | 4/2015 | Djupesland et al. | |
| 9,038,630 B2 | 5/2015 | Djupesland et al. | |
| 9,067,034 B2 | 6/2015 | Djupesland et al. | |

(56) References Cited

U.S. PATENT DOCUMENTS

| | | | |
|---|---|---|---|
| 9,072,857 B2 | 7/2015 | Djupesland | |
| 9,101,539 B2 | 8/2015 | Nagata et al. | |
| 9,119,932 B2 | 9/2015 | Djupesland | |
| 9,180,264 B2 | 11/2015 | Young et al. | |
| 9,272,104 B2 | 3/2016 | Djupesland | |
| 9,446,207 B2 | 9/2016 | Jung | |
| 2002/0017294 A1 | 2/2002 | Py | |
| 2002/0054856 A1 | 5/2002 | Jones | |
| 2002/0092520 A1* | 7/2002 | Casper | B05B 11/062 128/200.22 |
| 2003/0017119 A1 | 1/2003 | Rabinowitz et al. | |
| 2003/0158527 A1 | 8/2003 | Mezzoli | |
| 2003/0217748 A1 | 11/2003 | Giroux | |
| 2004/0068222 A1 | 4/2004 | Brian | |
| 2004/0217196 A1* | 11/2004 | Yurek, Jr. | F16L 37/0841 239/289 |
| 2004/0238574 A1 | 12/2004 | Merk et al. | |
| 2005/0023376 A1 | 2/2005 | Anderson | |
| 2005/0028812 A1 | 2/2005 | Djupesland | |
| 2005/0036985 A1 | 2/2005 | Ensoli | |
| 2005/0098172 A1 | 5/2005 | Anderson | |
| 2005/0142072 A1 | 6/2005 | Birch et al. | |
| 2005/0209553 A1* | 9/2005 | Landau | A61M 5/30 604/72 |
| 2005/0274378 A1 | 12/2005 | Bonney et al. | |
| 2006/0107957 A1 | 5/2006 | Djupesland | |
| 2006/0219813 A1 | 10/2006 | Morrison | |
| 2006/0240092 A1 | 10/2006 | Breitenkamp et al. | |
| 2006/0289006 A1 | 12/2006 | Williams et al. | |
| 2007/0029796 A1* | 2/2007 | Bibby | F16L 37/0985 285/308 |
| 2007/0056585 A1 | 3/2007 | Davies et al. | |
| 2007/0068514 A1 | 3/2007 | Giroux | |
| 2007/0074722 A1 | 4/2007 | Giroux et al. | |
| 2007/0119451 A1 | 5/2007 | Wang et al. | |
| 2007/0131224 A1 | 6/2007 | Giroux | |
| 2007/0172517 A1 | 7/2007 | Ben Sasson et al. | |
| 2007/0202051 A1 | 8/2007 | Schuschnig | |
| 2008/0054099 A1 | 3/2008 | Giroux et al. | |
| 2008/0163874 A1 | 7/2008 | Djupesland | |
| 2008/0178871 A1 | 7/2008 | Genova et al. | |
| 2008/0305077 A1 | 12/2008 | Frey et al. | |
| 2009/0066079 A1* | 3/2009 | Miros | F16L 37/248 285/124.5 |
| 2009/0320832 A1 | 12/2009 | Djupesland | |
| 2010/0074959 A1 | 3/2010 | Hansom et al. | |
| 2011/0045088 A1* | 2/2011 | Tsutsui | A61M 15/0081 424/490 |
| 2011/0053859 A1 | 3/2011 | Deadwyler et al. | |
| 2012/0195959 A1 | 8/2012 | Ishii | |
| 2012/0266883 A1* | 10/2012 | Taylor | C01B 13/0259 128/205.12 |
| 2014/0062080 A1* | 3/2014 | Battisti | F16L 37/086 285/86 |
| 2014/0083424 A1 | 3/2014 | Haekman et al. | |
| 2014/0170220 A1 | 6/2014 | Cartt et al. | |
| 2014/0343494 A1 | 11/2014 | Hoekman et al. | |
| 2015/0057287 A1 | 2/2015 | Cook et al. | |
| 2015/0167878 A1* | 6/2015 | Liu | F16L 37/0841 285/313 |
| 2015/0176741 A1* | 6/2015 | Juan | E03C 1/086 285/8 |
| 2015/0216823 A1 | 8/2015 | Chattehee | |
| 2015/0258178 A1 | 9/2015 | Gong | |
| 2015/0314085 A1 | 11/2015 | Banoun | |
| 2016/0001022 A1* | 1/2016 | Djupesland | A61M 15/085 128/203.18 |
| 2016/0058960 A1 | 3/2016 | Papania et al. | |
| 2016/0101245 A1* | 4/2016 | Hoekman | A61M 15/0035 264/537 |
| 2016/0228433 A1 | 8/2016 | Haruta et al. | |
| 2016/0287816 A1* | 10/2016 | Eksouzian | A61M 11/042 |
| 2017/0000999 A1* | 1/2017 | Dennis | A61M 39/1011 |
| 2017/0007788 A1 | 1/2017 | Brewer | |
| 2017/0043109 A1 | 2/2017 | Hoekman et al. | |
| 2018/0256836 A1 | 9/2018 | Hoekman et al. | |
| 2019/0151573 A1* | 5/2019 | Lee | A61M 15/0031 |
| 2019/0242509 A1* | 8/2019 | Klein | F16L 37/0987 |
| 2019/0383432 A1* | 12/2019 | Greco | F16L 41/021 |

FOREIGN PATENT DOCUMENTS

| | | | | |
|---|---|---|---|---|
| CN | 103917265 A | 7/2014 | | |
| DE | 19518580 A1 | 11/1996 | | |
| DE | 102013100473 A1 | 7/2014 | | |
| EP | 1165044 A2 | 1/2002 | | |
| GB | 806284 A | 12/1958 | | |
| GB | 1517642 A | 7/1978 | | |
| JP | H 08322934 A | 12/1996 | | |
| JP | 2014530637 A | 11/2014 | | |
| JP | 2016520378 A | 7/2016 | | |
| JP | 2018527099 A | 9/2018 | | |
| WO | WO 1986001731 A1 | 3/1986 | | |
| WO | WO 1999013930 A1 | 3/1999 | | |
| WO | WO-9958180 A1 * | 11/1999 | | A61M 15/0028 |
| WO | WO 2000054887 A1 | 9/2000 | | |
| WO | WO 2001036033 A2 | 5/2001 | | |
| WO | WO 2002009707 A1 | 2/2002 | | |
| WO | WO 2007012853 A1 | 2/2007 | | |
| WO | WO 2008059385 A2 | 5/2008 | | |
| WO | WO 2014/165694 A2 | 10/2014 | | |
| WO | WO 2014/179228 A1 | 11/2014 | | |
| WO | WO 2019/104205 A1 | 5/2019 | | |

OTHER PUBLICATIONS

Baron, "Orally Inhaled Dihydroergotamine; Reviving and Improving a Classic", Future Neurology, May 2011, 11 pages.

Banks, W. A. et al. "Brain Uptake of the Glucagon-Like Peptide-1 Antagonist Exendein (9-39) after Intranasal Administration." The Journal of Pharmacology and Experimental Therapeutics, vol. 309, No. 2, May 2004, pp. 469-475.

Constantino, et al., "Intranasal administration of acetylcholinesterase inhibitors", BMC Neuroscience, Dec. 10, 2008, 3 pages.

Ding, X. et al. "Olfactory Mucosa: Composition, Enzymatic Localization, and Metabolism." Handbook of Olfaction and Gustation, $2^{nd}$ Edition, 2003, pp. 51-73.

European Patent Office, EP Office Action for 14727320.5, dated Nov, 9, 2016, 6 pages.

European Patent Office, EP Search Report for 09707800.0 dated Jul. 1, 2015, 12 pages.

European Patent Office, EP Search Report for 11818832.5 dated Sep. 24, 2014, 6 pages.

Hanson, et al., "Intranasal delivery of growth differentiation factor 5 to the central nervous system", Drug Delivery, 19(3):449-54, Feb. 2012, 7 pages.

Henry, R. J. et al. "A Pharmacokinetic Study of Midazolam in Dogs: Nasal Drop vs. Atomizer Administration," Pediatric Dentistry, vol. 20, No. 5, Sep. 1, 1998, pp. 321-326.

Hoekman, J.D., "The Impact of Enhanced Olfactory Deposition and Retention on Direct Nose-to-Brain Drug Delivery", UMI Dissertation Publishing, Apr. 11, 2011, 181 pages.

Kumar, et al., "Nasal Dmg Delivery: A Potential Route for Brain Targeting" The Pharma Innovation Journal, vol. 2, No. 1, Mar. 2013, 9 pages.

Mathison, S. et al. "Nasal Route for Direct Delivery of Solutes to the Central Nervous System: Fact or Fiction?" Journal of Drug Targeting, vol. 5, No. 6, 1998, pp. 415-441.

Morrison, E. E. et al. "Morphology of the Human Olfactory Epithelium." J. Comp. Neurol. vol. 297, No. 1, pp. 1-13.

Ozsoy, et al., "Nasal Delivery of High Molecular Weight Drugs", Molecules Journal, Sep. 23, 2009, 26 pages.

Pardridge, W. M. "Targeting Neurotherpaeutic Agents Through the Blood-Brain Barrier." Arch. Neurol., vol. 59, No. 1, Jan. 2002, pp. 35-40.

Pardridge, W. M. "The Blood-Brain Barrier and Neurotherapeutics." NeuroRX, vol. 2, No. 1, Jan. 2005, pp. 1-2.

(56) References Cited

OTHER PUBLICATIONS

Pardridge, W. M. "The Blood-Brain Barrier: Bottleneck in Brain Dmg Development." NeuroRX, vol. 2, Jan. 2005, pp. 3-14.
Parvathi, "Intranasal Dmg Delivery to Brain: An Overview," published in the International Journal of Research in Pharmacy and Chemistry 2012, 2(3), 7 pages.
PCT International Search Report and Written Opinion, PCT Application No. PCT/US2011/048435, dated Mar. 27, 2012, 14 pages.
PCT International Search Report, PCT Application No. PCT/US/2009/033468, dated Dec. 2, 2009, 5 pages.
Renner, et al., "Intranasal delivery of growth differentiation factor 5 to the central nervous system," Drug Delivery, Feb. 2012, 7 pages.
Sakane, T. et al. "Transport of Cephalexin to the Cerebrospinal Fluid Directly from the Nasal Cavity." Journal of Pharmacy and Pharmacology, vol. 43, No. 6, Jun. 1991, pp. 449-451.
Stevens, et al., "Systemic and Direct Nose-to-Brain Transport Pharmacokinetic Model for Remoxipride after Intravenous and Intranasal Administration", in "Drug Metabolism and Disposition", The American Society for Pharmacology and Experimental Therapeutics, 2011, vol. 39, No. 12, 8 pages.
Talegaonkar, et al., "Intranasal delivery: an approach to bypass the blook brain barrier", Indian J Pharmacol, Jun. 2004, vol. 36, Issue 3, 8 pages.
Westin et al, "Direct Nose to Brain Transfer of Morphine After Nasal Administration to Rats", Pharmaceutical Research, vol. 23, No. 3, Mar. 2006, 8 pgs.
Westin, "Olfactory Tranfser of Analgesic Drugs After Nasal Administration", Digital Comprehensive Summaries of Uppsala Dissertations from the Faculty of Pharmacy 55, May 11, 2007, 66 pages.
Yamada, et al., "Nose-to-brain delivery of TS-002, prostaglandin D2 analogue", Journal of Drug Targeting, Jan. 2007, 9 pages.
Yimam, et al., "Effects of lipid association on lomustine (CCNU) administered intracerebrally to syngeneic 36B-10 rat brain tumors", Cancer Letters 244(2), Dec. 2006, 9 pages.
Ying, "The nose may help the brain: intranasal drug delivery for treating neurological diseases" Future Medecine, 3(1), Jan. 2008, 4 pages.
Zhang, et al, "The brain targeting efficiency following nasally applied MPEG-PLA nanoparticles in rats", Journal of Dmg Targeting, Jun. 2006, 11 pages.
Chinese Patent Office, Office Action, Chinese Patent Application No. 201980092137.5, dated Nov. 24, 2021, seven pages, (with concise explanation of relevance).
European Patent Office, Partial Supplementary Search Report, European Patent Application No. 19907973.2, dated Aug. 30, 2022, 12 pages.
PCT International Search Report and Written Opinion, International Application No. PCT/US2019/066921, dated Feb. 24, 2020, 18 Pages.
Chilean National Institute of Industrial Property, Office Action, Chilean Patent Application No. 202101755, dated Dec. 7, 2022, 17 pages.
China National Intellectual Property Administration, First Office Action, Chinese Patent Application No. 201980092137.5, dated Nov. 24, 2021, 11 pages.
China National Intellectual Property Administration, Notice to Grant, Chinese Patent Application No. 201980092137.5, dated Jun. 20, 2022, five pages.
European Patent Office, Extended European Search Report, European Patent Application No. 19907973.2, dated Nov. 30, 2022, 11 pages.
The Israeli Patent Office, Notice Before Acceptance, Israeli Patent Application No. 284362, dated Nov. 21, 2022, five pages.
The Japan Patent Office, Office Action, Japanese Application No. 2021-539346, dated Nov. 22, 2022, four pages.

* cited by examiner

NASAL DRUG DELIVERY DEVICE WITH DETACHABLE NOZZLE

CROSS REFERENCE TO RELATED APPLICATIONS

This application claims the benefit of priority to U.S. Provisional Patent Application No. 62/788,093, filed on Jan. 3, 2019, entitled "Nasal Drug Delivery Device" which is incorporated herein by reference in its entirety for all purposes.

BACKGROUND

This disclosure relates generally to a drug delivery device, and specifically to a nasal drug delivery device for delivering drugs to an upper nasal cavity of a user.

The central nervous system (CNS) includes the brain, the brain stem, and the spinal cord. The CNS is isolated from the external world by several membranes that both cushion and protect the brain, the brain stem, and the spinal cord. For example, the membranes that form the blood-brain barrier (BBB) protect the brain from certain contents of the blood. The blood-cerebrospinal fluid barrier (BCSFB) protects other portions of the CNS from many chemicals and microbes.

Traditional methods for delivering compounds to the CNS are typically invasive. For example, a pump implanted in the skull, such as an intracerebroventricular pump, can deliver a variety of compounds to the brain. However, implanting such a pump requires brain surgery, which can entail a variety of serious complications. Certain compounds, for example epidural painkillers, can be injected directly through the protective membrane into the CNS. However, such injection is impractical for most compounds.

Intranasal administration has traditionally focused on the distribution of drug solutions as a mist for topical delivery to the nasal epithelium. Because of the nasal cavity's easily accessed vascular bed, nasal administration of medications has focused the delivery of medications either locally to the nasal cavity or directly to the blood stream.

Much of the current brain research is focused on the enhancement of the drug being delivered to the brain by various formulations. The traditional approaches to improve uptake of compounds to the brain by formulation enhancement include (1) mucoadhesive formulations; 2) penetration enhancers; 3) liposomes; 4) vasoconstrictors; and 5) nanoparticles. Examples of various compounds with have enhanced formulations include various cytokines, for example, tumor necrosis factors, interleukins, and interferons discussed in U.S. Pat. No. 6,991,785 and growth and differentiation factor-5 (GDF-5) and related proteins discussed in US Publication No. 20100074959.

Targeting of drugs to the central nervous system (CNS) is a challenging task. A great number of drugs, including biotechnology products, are candidates for treatment of CNS diseases, but drug delivery is a problem for brain targeting. A limitation in the treatment of brain tumors is that less than 1% of most therapeutic agents administered systemically are able to cross the BBB. The transport of small molecules across the BBB is the exception rather than the rule, and 98% of all small molecules do not cross the BBB (Pardride, NeuroRx. 2005 January; 2(1): 1-2. 2005); approximately 100% of large-molecule drugs or genes do not cross the BBB (Pardride, NeuroRx. 2005 January; 2(1): 1-2. 2005). The BBB allows small (about less than 500 Da), lipophilic molecules from the bloodstream to enter the CNS (Pardridge, Arch Neurol. 2002; 59:35-40). Many larger therapeutic agents are prevented from reaching the brain for treating CNS disorders such as but not limited to Parkinson's disease, Alzheimer's disease, depression, stroke, and epilepsy (Pardridge, NeuroRx. 2005 January; 2(1): 3-14). Disorders including autism, lysosomal storage disorders, fragile X syndrome, ataxis, and blindness, are serious disorders where there is little effective treatment. In many of these cases, the gene underlying the disease is known, but BBB delivery is the rate-limiting problem in gene therapy or enzyme replacement therapy, and no therapeutics have been developed. Drug delivery of therapeutic compounds, for example proteins, faces several challenges because of their instability, high enzymatic metabolism, low gastrointestinal absorption, rapid renal elimination, and potential immunogenicity.

There is a need for devices that can deliver compounds to the upper nasal cavity for direct nose-to-brain delivery. Certain existing nasal drug delivery devices do not adequately propel the drug from the device. Inconsistent propulsion of drug due to inconsistent user actuation is also far from optimal. For example, some existing devices are manually actuated and may be used in conjunction with a manual pump, such that the actuation of the device is dependent on a user's rate and/or strength of actuation of the pump. Some existing devices require the user to coordinate their breathing with device actuation, which can produce variable results due to differences in a user's breath power. In addition, some drug products are in an encapsulated form, which requires the capsule to be opened or punctured to administer the drug, which may result in particulate matter from the capsule contaminating the drug. Even further, in a metered dose inhaler (MDI) type device, some drug products do not readily mix and/or stay suspended with propellants.

Better mechanisms for administering desired agents to the brain, brain stem, and/or spinal cord are needed.

SUMMARY

A device for delivering a compound to the upper nasal cavity is described. In one embodiment, the device includes a housing body comprising an actuator, a stem, and a release button. The actuator is configured to move relative to the housing body, where actuation of the actuator is configured to actuate a canister thereby releasing a contained propellant. The stem protrudes from the housing body and comprises a mating interface that mates with a nozzle containing the compound. The release button is positioned within the housing body and moves relative to the housing body. The release button is directly connected to a securing mechanism that couples the nozzle to the mating interface, where actuation of the release button decouples the nozzle from the mating interface.

In one embodiment, the nozzle comprises a nozzle body, a diffuser, an outlet orifice, a removable seal, and a receiving cavity. The nozzle body comprises a channel that extends between a proximal end and a distal end of the nozzle body, and the diffuser is positioned within the channel. The outlet orifice is disposed at a distal end of the channel, and the removable seal is positioned across the outlet orifice. The compound is contained within the channel between the diffuser and the removable seal, and the removable seal may be removed by a user before the compound is administered. The receiving cavity is disposed about an outer surface of the nozzle body and receives a reciprocal mating interface of the device.

Upon user actuation of the device, the released propellant travels to the channel of the nozzle body, contacts the diffuser, and propels the compound out the outlet orifice for delivery into the upper nasal cavity. In this configuration, the device administers the dose to the upper nasal cavity independent of the user's breathing and/or user's rate and/or strength of actuation. In addition, the nozzle may be coupled to and decoupled from the housing body. The nozzle is used to deliver a single dose of the compound, such that after dispensing the dose, the nozzle may be removed from the housing body and a new nozzle may be attached for delivering a future dose. This configuration maintains the integrity of the compound contained within the detachable nozzle and consistently administers the dose to the upper nasal cavity.

Figure 1A:
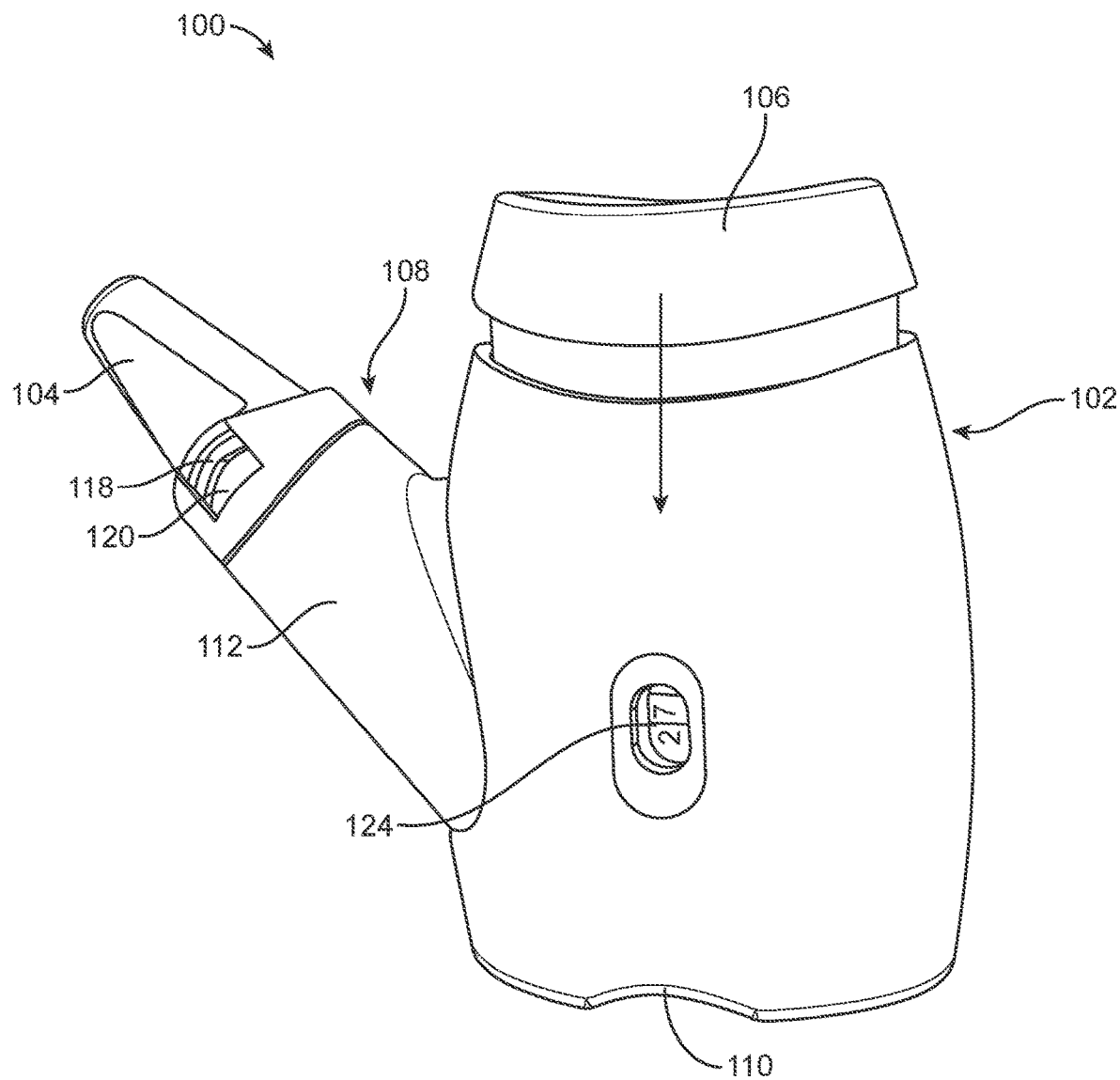
FIG. 1A illustrates a perspective view of a nasal drug delivery device, in accordance with one or more embodiments.

The figures depict embodiments of the present disclosure for purposes of illustration only. One skilled in the art will readily recognize from the following description that alternative embodiments of the structures and methods illustrated herein may be employed without departing from the principles, or benefits touted, of the disclosure described herein.

DETAILED DESCRIPTION

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise:

As used herein the specification, "a" or "an" may mean one or more.

A "diagnostic agent" refers to and encompasses an atom, molecule, or compound that is useful in diagnosing a disease. Diagnostic agents include, but are not limited to, radioisotopes, dyes, contrast agents, fluorescent compounds or molecules and enhancing agents (e.g., paramagnetic ions). A non-radioactive diagnostic agent is a contrast agent suitable for magnetic resonance imaging, computed tomography, or ultrasound. The diagnostic agent can be used to perform positron emission tomography (PET), MRI, X-ray, CT, ultrasound, operative, intravascular, laparoscopic, or endoscopic procedure.

A "diffuser" refers to and encompasses a component for dispersing or deflecting a compound in various directions.

A "frit" is one type of a diffuser and shall refer to and encompass a porous member or filter.

An "imaging agent" refers to and encompasses an atom, molecule or compound that is useful in detecting physical changes or produces images of internal body tissues. In some aspects, the imaging agent may be a diagnostic agent.

A "propellant" shall refer to and encompass a compound that acts as a vehicle for creating propulsion or thrust.

The term "therapeutically effective amount" refers to and encompasses an amount of a drug effective to treat a disease or disorder in a mammal. In one aspect, the therapeutically effective amount refers to a target CNS concentration that has been shown to be effective in, for example, slowing disease progression. Efficacy can be measured in conventional ways, depending on the condition to be treated.

The term "treatment" and "treat", and the like, refers to and encompasses therapeutic or suppressive measures for a disease or disorder leading to any clinically desirable or beneficial effect, including, but not limited to, alleviation or relief of one or more symptoms, regression, slowing or cessation of progression of the disease or disorder. Treatment can be evidenced as a decrease in the severity of a symptom, the number of symptoms, or frequency of relapse.

A "user" or "subject" shall refer to and encompass a human or other animal. For example, the animal may be a primate or a non-primate and may include a rabbit, bovine, equine, pig, rat, mouse, dog or cat.

The device may be used in treatment, prevention, palliative care for humans and veterinary purposes. The device may be used in research and industrial uses. For example, the device may be used to deposit compound in agricultural settings.

When trade names are used herein, applicants intend to independently include the trade name product formulation, the generic drug, and the active pharmaceutical ingredient(s) of the trade name product.

For clarity of disclosure, and not by way of limitation, the detailed description of the invention is divided into the subsections which follow.

Intranasal administration of compounds to the upper nasal cavity offers several advantages over traditional surgical, intravenous or oral routes for administration across the blood brain barrier (BBB). The upper nasal cavity may include the olfactory region and the middle and superior turbinate regions, among other regions within the nasal cavity. Intranasal administration to specifically the olfactory region avoids gastrointestinal destruction and hepatic first pass metabolism, such as destruction of drugs by liver enzymes, allowing more drug to be cost-effectively, rapidly, and predictably bioavailable than if it were administered orally. Intranasal administration provides ease, convenience and safety. Intranasal drug administration is generally painless (taking into consideration that pain may be a subjective measurement which varies by patient) and does not require sterile technique, intravenous catheters or other invasive devices, and is generally immediately and readily available for all patients. Intranasal administration can rapidly achieve therapeutic brain and spinal cord drug concentrations.

Nasally administered compounds contact the upper olfactory region and molecular transport occurs directly across this tissue and into compartments of the central nervous system. (Henry, R. J., et al., Pediatr Dent, 1998. 20(5): p. 321-6; Sakane, T., et al., J Pharm Pharmacol, 1991. 43(6): p. 449-51; Banks, W. A., et al., J Pharmacol Exp Ther, 2004. 309(2): p. 469-75; Westin, et al., Pharm Res, 2006. 23(3): p. 565-72). The olfactory mucosa is located in the upper nasal cavity, just below the cribriform plate of the skull. It contains olfactory cells which traverse the cribriform plate and extend up into the cranial cavity. When compounds come in contact with this specialized mucosa, they are rapidly transported directly into the brain, they bypass the BBB, and are rapidly transported directly into the central nervous system, often faster than if the compound is given intravenously.

The olfactory mucosa includes the olfactory epithelium. The olfactory epithelium is located at the top of the nose between the superior turbinate and the roof of the nasal cavity, just beneath the cribriform plate of the ethmoid bone. In humans, it covers about 10 to about 20 $cm^2$, or about 8% of the total nasal surface area, and is composed of four main cell types: epithelial cells, olfactory receptor neurons, supporting cells, and basal cells. (Mathison S. et al., (1998) Journal of Drug Targeting 5: 415-441). Although 3% of the nasal cavity is occupied by olfactory epithelium (Morrison and Costanzo, 1990), this route is direct, since the olfactory neurons do not have a synapse between the receptive element and the afferent path (Ding and Dahl, 2003). The olfactory epithelium is more than twice the depth of the respiratory epithelium, with the olfactory nerve cell bodies typically located in the middle and deeper regions of the epithelium while nuclei of the supporting cells are organized in a single layer closer to the mucosal surface. Tight junctions exist between the supporting cells and between the supporting cells and olfactory nerve cells. Morrison E. E, et al. (1992) Journal of Comparative Neurology 297(1): 1-13.

When a nasal drug formulation is delivered deep and high enough into the nasal cavity, the olfactory mucosa is reached and drug transport into the brain and/or CSF via the olfactory receptor neurons occurs. The transfer of compounds from the nose to the brain is referred to as the nose-brain pathway. The nose-brain pathway has implications when centrally acting medications such as but not limited to sedatives, anti-seizure drugs, and opiates are delivered nasally. The present device allows for delivery via the nose-brain pathway allowing for nearly immediate delivery of nasal medications to the central nervous system and brain, by-passing the blood brain barrier.

The current challenge in nose-to-brain drug delivery is also due to the complex architecture of the nose, which is naturally designed to channel drugs into the lower nasal airway toward the lungs making it difficult for drugs to reach the olfactory region. Most of the drug dispensed from traditional nasal devices such as sprayers or pumps is subjected to the natural air movement in the nasal cavity towards the esophagus. The majority of the spray dispensed from traditional devices encounters the natural downward airflow displacement within the nasal cavity. The remaining fraction from traditional devices is found in the respiratory epithelium and cleared by the mucocilliary clearance mechanism or absorbed into the blood stream. While nasal catheter instillation and nose drops are less impacted by this natural downward air movement, it requires subjects to be in a supine position, is often associated with user discomfort, and is not optimal for frequent clinical administration.

Moreover, a reservoir of residual air exists at the top of the nasal cavity that is not removed during normal respiration, thus remaining in the olfactory region and acting as a barrier to deposition. This residual air must be displaced in order to deliver aerosolized drug to the olfactory epithelium in the upper nasal cavity in a consistent manner. The device described herein delivers a majority of the aerosolized drug to the upper part of the nasal cavity to increase exposure of the drug at the olfactory epithelium, a site of nose-to-brain pathway, by both avoiding the natural downward air movement and displacing the residual air of the upper nasal cavity.

The device herein advantageously and consistently deposits a large fraction of dose into the more distal parts of the nasal cavity such as the olfactory region. A drug product (also referred to herein as drug formulation, drug compound, or intranasal dosage form) is propelled from the device with a velocity into the nasal cavity.

Figure 1B:
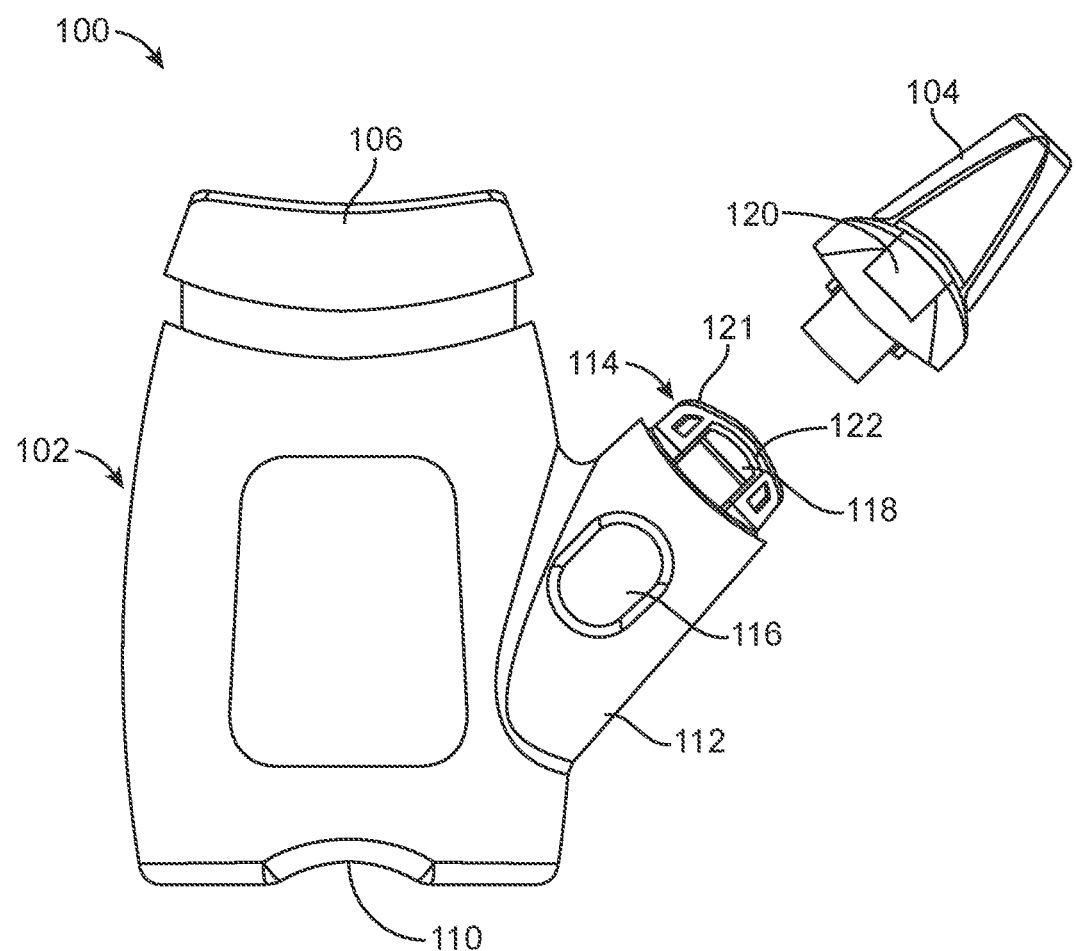
FIG. 1B illustrates a side view of the device of FIG. 1A with a nozzle detached, in accordance with one or more embodiments.

FIGS. 1A and 1B illustrate a perspective view of a nasal drug delivery device 100 and a side view of the device 100 with the nozzle detached, respectively, in accordance with one or more embodiments. The device 100 is designed to deliver a drug compound to an upper nasal cavity of a user. The drug compound may be a liquid, powder, or some combination thereof. In various embodiments, the device 100 may deliver a single dose or a multi-dose, may be single-use or reusable, may be manually actuated and propellant-driven, or some combination thereof. In the embodiments of FIGS. 1A and 1B, the device 100 is propellant-driven, delivers a single dose, and may be reused to deliver several individual doses. In the embodiments of FIGS. 1A and 1B, the device 100 comprises a housing body 102, a nozzle 104 that contains the drug compound, an actuator 106, and a coupling interface 108 that couples the nozzle 104 to the housing body 102. The nozzle 104 may be coupled to the housing body 102 for delivery of the dose, as shown in FIG. 1A, and may be decoupled from the housing body 102, as shown in FIG. 1B, after the drug compound is dispensed into an upper nasal cavity of the user. A new nozzle 104 may be coupled to the housing body 102 for delivery of a subsequent dose.

The housing body 102 represents the body of the device 100. The housing body 102 is designed to be held in a hand of a user and may include one or more ergonomic features for the comfort of the user. For example, in the embodiment of FIGS. 1A and 1B, the housing body 102 includes an indentation 110 that allows a user to comfortably hold and engage the device 100 with the fingers, for example a thumb positioned on the indentation 110 and one or more fingers positioned on top of the actuator 106. In the embodiment of FIGS. 1A and 1B, the housing body 102 is composed of two "clamshells" pieces that conceal an internal assembly of the device 100 and retain all of the components in alignment to ensure functionality. A top portion of the housing body 102 couples with the actuator 106 such that the actuator 106 moves relative to the housing body 102. In this configuration, the user may apply a vertical downward force (in the direction of the arrow) to the actuator 106 to actuate the device 100. In alternate embodiments, the housing body 102 and the actuator 106 may be arranged in a different orientation such that the user applies a vertical upward force, a horizontal force, a diagonal force, or some combination thereof to the actuator 106 to actuate the device 100. A stem 112 of the housing body 102 couples to the nozzle 104 via the coupling interface 108.

The nozzle 104 contains the drug compound. In the embodiment of FIGS. 1A and 1B, the nozzle 104 is a single-use nozzle, where the nozzle 104 holds a single dose and may be replaced after each use. The nozzle 104 includes a channel (shown in FIG. 2) that holds the drug compound and an outlet orifice at a distal end (shown in FIG. 2) of the nozzle 104 through which the drug compound may exit the nozzle 104. Housed within the housing body 102 is a propellant canister (shown in FIG. 2) that is in fluid communication with the channel of the nozzle 104, such that propellant released from the canister travels through the nozzle channel and propels the drug compound out the outlet orifice. In the embodiments of FIGS. 1A and 1B, the nozzle 104 may be coupled to and decoupled from the stem 112 via the coupling interface 108.

The actuator 106 is manually actuated by a user to dispense a dose from the nozzle 104. The actuator 106 moves relative to the housing body 102 (e.g., slides, translates, rotates, or other similar motion). In the embodiment of FIGS. 1A and 1B, the actuator 106 translates in a vertical motion, represented by the direction of the arrow. The actuator 106 is coupled to the propellant canister (shown in FIG. 2) housed within the housing body 102. In this configuration, actuation of the actuator 106 causes actuation of the propellant canister, thereby releasing propellant that travels through the housing body 102 to the channel of the nozzle 104 and propels the drug compound out the outlet orifice of the nozzle 104.

Figure 2:
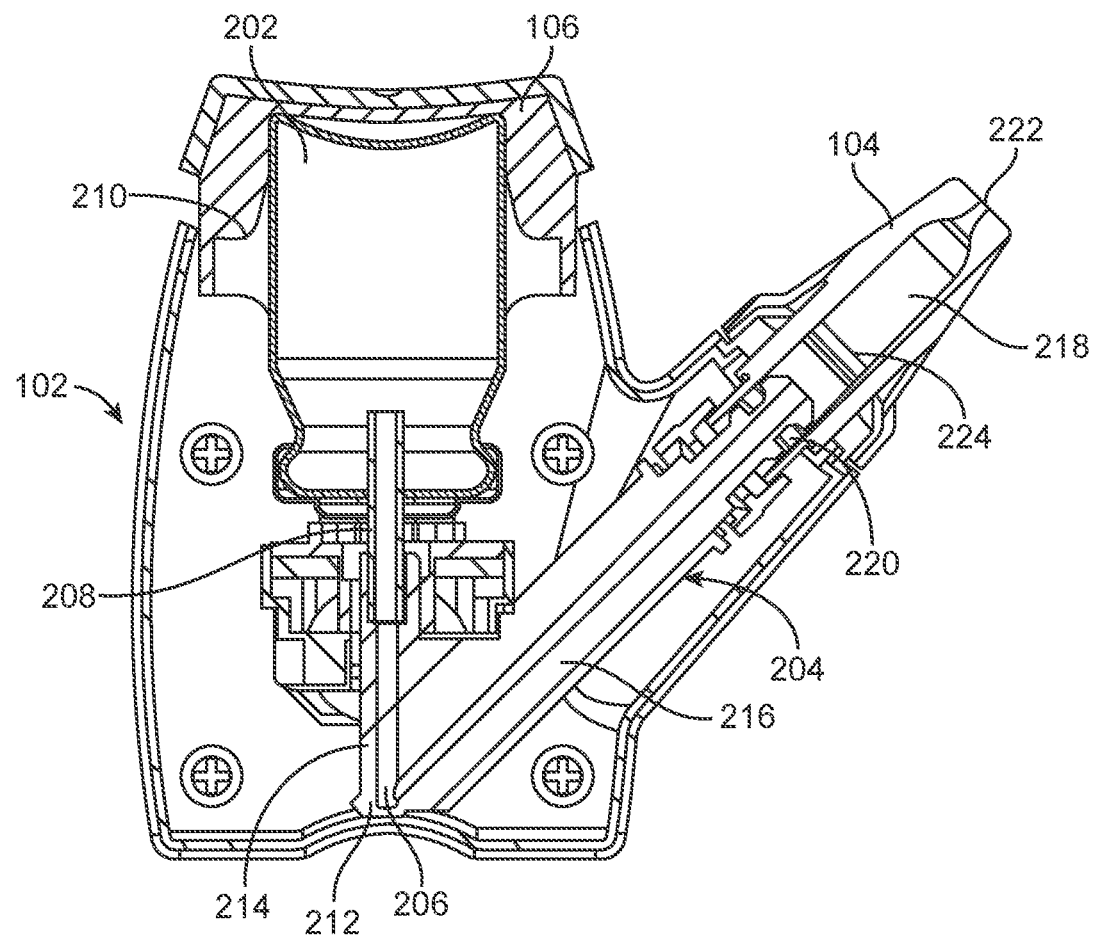
FIG. 2 illustrates a cross-sectional view of the device of FIGS. 1A and 1B, in accordance with one or more embodiments.

The coupling interface 108 couples the nozzle 104 to the housing body 102 and decouples the nozzle 104 from the housing body 102 upon actuation of a release button 116. In the embodiment of FIG. 2, the coupling interface 108 comprises a mating interface 114 on the stem 112, a reciprocal mating interface (shown in FIGS. 4-5) on the nozzle 104, the release button 116 which is directly connected to a securing latch 118, and an opening 120 that receives the securing latch 118. Specifically, the mating interface 114 of the stem 112 couples the reciprocal mating interface of the nozzle 104.

In the embodiments of FIGS. 1A and 1B, the mating interface 114 comprises one or more protruding tabs 121, and the reciprocal mating interface is a receiving cavity, where the receiving cavity receives the one or more protruding tabs 121. In alternate embodiments, the configuration of the receiving cavity and protruding tabs 121 may be reversed (e.g., on opposite components). The mating interface 114 comprises one or more holes 122 such that the securing latch 118 protrudes through a respective hole 122. To couple the nozzle 104 to the housing body 102, the nozzle 104 is positioned onto the stem 112 such that the receiving cavity receives the one or more protruding tabs 121. The opening 120 receives the securing latch 118, which secures the nozzle 104 to the housing body 102. In the embodiments of FIGS. 1A and 1B, the securing latch 118 is directly connected to the release button 116, where actuating the release button 116 causes movement of the securing latch 118. To decouple the nozzle 104 from the housing body 102, the release button 116 is actuated, and the securing latch 118 is displaced from the opening 120. The coupling mechanism is discussed in further detail in FIGS. 6-7. In one embodiment, an outer surface of the nozzle 104 and an outer surface of the stem 112 are flush when coupled together.

In some embodiments, the device 100 includes a dose counter 124. The dose counter 124 tracks the number of actuations of the propellant canister, such that a user may be aware of the amount of propellant remaining in the propellant canister. For example, a propellant canister may have a capacity for distributing propellant for a certain number of doses. In some embodiments, the propellant canister may be replaced with a new propellant canister, such that the device 100 may be reused. In one aspect, when a MDI device is actuated, a discrete amount of pressurized HFA fluid is released. The MDI may contain between about 30 to about 300 actuations, inclusive of endpoints, of HFA propellant. The amount of fluid propellant released upon actuation may be between about 20 microliters (µl) and about 200 microliters (µl) inclusive of endpoints, of liquid propellant.

FIG. 2 illustrates a cross-sectional view of the device of FIGS. 1A and 1B, in accordance with one or more embodiments. The cross-sectional view exposes the internal assembly within the housing body 102 and the mating interfaces between the nozzle 104 and the housing body 102. In the embodiment of FIG. 2, the internal assembly comprises a propellant canister 202 and a junction 204 that couples to the nozzle 104, the junction 204 having a propellant channel 206.

The propellant canister 202 contains propellant. In one embodiment, the propellant may be pressurized. The propellant is a fluid, for example, a liquid or gas. In one aspect, the propellant is a liquid. In another aspect, the propellant is a gas. Propellants include pharmaceutically suitable propellants. Some examples of pharmaceutically suitable propellants include hydrofluoroalkane (HFA) including but not limited to HFA, HFA 227, HFA 134a, HFA-FP, HFA-BP and the like HFA's. In one aspect, the propellant is liquid HFA. In another aspect, the propellant is gaseous HFA. Additional examples of suitable propellants include nitrogen or cholorofluorocarbons (CFC). Additionally, propellants may be pressurized air (e.g. ambient air).

The canister 202 may be a metered dose inhaler (MDI) device that includes a pressurized canister and metering valve 208 (including stem) to meter the propellant upon actuation. In one embodiment, a pump fitment (not shown) secures the metered valve 208 to the canister 202 and holds both components in place during device 100 use. One series of embodiments of the pump fitment consists of securing interfaces that retain the pump fitment within the housing body 102, provide vertical displacement, and prevent rotation during installation of the canister 202. As shown in FIG. 2, the canister 202 is coupled to the actuator 106. A portion of the canister 202 is positioned within a cavity 210 of the actuator 106 such that movement of the actuator 106 causes actuation of the canister 202 (i.e., the canister 202 moves relative to the metering valve 208, thereby releasing propellant). In the embodiment of FIG. 2, the canister 202 is coupled to the junction 204 such that the metering valve 208 is in fluid communication with the propellant channel 206. In this configuration, the propellant in the canister 202 acts as a vehicle to deliver propulsion or thrust to expel the drug compound from the nozzle 104.

The junction 204 is an internal structure that couples the canister 202 to the nozzle 104. The propellant channel 206 extends through the junction 204, thereby creating a flow path from the canister 202 to the nozzle 104. As shown in FIG. 2, the junction 204 comprises a base 212, a first branch 214, and a second branch 216. The first branch 214 and the second branch 216 both extend from the base 212. In the embodiment of FIG. 2, the first branch 214 couples to the metering valve 208, and the second branch 216 couples to the nozzle 104. The propellant channel 206 extends from the proximal end of the first branch 214 to the distal end of the second branch 216 and is in fluid communication with the canister 202 and the nozzle 104. Propellant released from the canister 202 travels through the propellant channel 206 to the nozzle 104. In alternate embodiments, the junction 204 may have a varying number of branches that may be in a different arrangement. For example, an angle between the branches may vary between 0 to 180 degrees. In one series of embodiments, the angle is 30 degrees, 35 degrees, 40 degrees, 45 degrees, 50 degrees, 55 degrees, 60 degrees, inclusive of endpoints and intervening degrees.

The distal end of the second branch 216 couples with the nozzle 104. Specifically, the distal end of the second branch 216 is inserted into a nozzle channel 218 when the nozzle 104 is positioned onto the stem 112. The distal end of the second branch 216 may have a tapered end and/or a chamfer to facilitate insertion into the nozzle channel 218. In the embodiment of FIG. 2, the distal end of the second branch 216 comprises a sealing ring 220 that creates an airtight seal between the junction 204 and an internal surface of the nozzle channel 218. The sealing ring 220 may be an o-ring or an x-ring (lubricated or non-lubricated). In the embodiment of FIG. 2, the sealing ring 220 is an x-ring, which has a lower insertion force than an o-ring when the distal end of the second branch 216 is inserted into the nozzle channel 218. Stated differently, an x-ring does not have to deform as much as an o-ring to be positioned within the nozzle channel 218. This configuration decreases both the stiffness of the sealing ring 220 and the potential friction created by the sealing ring 220, which enables a user to easily couple and decouple the nozzle 104 to and from the device 100, thus improving the user experience. In addition, the x-ring is non-lubricated, which prevents lubricant from leeching onto other components of the device 100 or a user of the device.

As shown in FIG. 2, the nozzle 104 comprises the nozzle channel 218, an outlet orifice 222, and a diffuser 224. The nozzle channel 218 extends between a proximal end and a distal end of the nozzle 104. The outlet orifice 222 is an opening at the distal end of the nozzle 104. The diffuser 224 is positioned within the channel such that the diffuser 224 spans across the diameter of the nozzle channel 218. The drug compound is positioned within the nozzle channel 218 between the diffuser 224 and the outlet orifice 222. In this configuration, the nozzle channel 218 is in fluid communication with the propellant channel 206 such that propellant released from the canister travels through the propellant channel 206, into the nozzle channel 218, contacts the diffuser 224, and propels the drug compound out the outlet orifice 222.

The diffuser 224 diffuses propellant released from the canister 202. In one aspect, a majority of the propellant is diffused via the diffuser. In another aspect, a minority of the propellant is diffused via the diffuser. Majority refers to and encompasses at least 50 percent. Minority refers to and encompasses less than 50 percent. In another aspect, at least about 10%, 15%, 20%, 25%, 30%, 35%, 40%, 45%, 50%, 55%, 60%, 65%, 70%, 75%, 80%, 85%, 90%, 95%, 99% or about 100%, inclusive of endpoints, of the propellant is diffused via the diffuser. The diffuser 224 is in communication with the nozzle channel 218.

In some aspects, the diffuser 224 functions to convert propellant from a liquid to a gas. Specifically, the diffuser 224 expands the propellant from a liquid state to a gaseous state. In other aspects, the diffuser 224 functions to prevent the drug compound contained in the nozzle channel 218 from coming in contact with the canister 202. In another aspect, the diffuser acts as a one-way check valve. In other aspects, the diffuser 224 functions to convert propellant from a liquid to a gas and to prevent the compound contained in the nozzle channel 218 from coming into contact with the canister 202. In yet another aspect, the diffuser functions to increase the temperature of the propellant. In one aspect, the diffuser converts the liquid propellant into a gaseous state, which then aerosolizes the drug compound and propels the aerosolized drug compound through the nozzle channel 218 and out the outlet orifice 222.

An example of a diffuser 224 includes a frit, a plurality of frits, or a diffuser member or combinations thereof. In one aspect, the diffuser is a frit. In another aspect, the diffuser is a plurality of frits. In another aspect, the diffuser is a diffuser member.

In one aspect, the frit(s) are of any suitable size and shape and are formed using any suitable porous material of any suitable density. In one aspect, the frit is made of a hydrophobic material. In one aspect, the frit is made of an inert material to avoid chemically reacting with any of the compounds. The inert material may be metal or non-metal. In one aspect, the frit is composed of metal. In another aspect, the frit is composed of a non-metal. In one aspect, the inert material is sintered nickel. As one example, a frit formed using a porous stainless steel having a pore size in the range of approximately 1 micron to approximately 100 microns can be used. In another aspect the pore size is in the range of about 1 to about 10, about 10 to about 20, about 20 to about 30, about 30 to about 40, about 40 to about 50, about 50 to about 60, about 60 to about 70, about 70 to about 80, about 80 to about 90, about 90 to about 100 microns, inclusive of endpoints. In another aspect, the frit can be formed using aluminum foam. The number and size of the pores and the overall dimensions (e.g., diameter and thickness) of the frit are set to maximize surface area for vaporization while limiting pressure drops accompanying passage of vaporized propellant through the frit. The frit may be homogenously or heterogeneously porous. In certain aspects, the frit may be constructed of Teflon, glass, metal mesh, screen, porous metal, polyether ether ketone or another plastic material. In one aspect, the passage of liquid propellant through the increased surface area of the frit transitions the liquid to gas and increases the temperature of the resulting gas. In another aspect, the passage of gas propellant through the increased surface area of the frit increases the temperature of the gas.

Figures 3A, 3B:
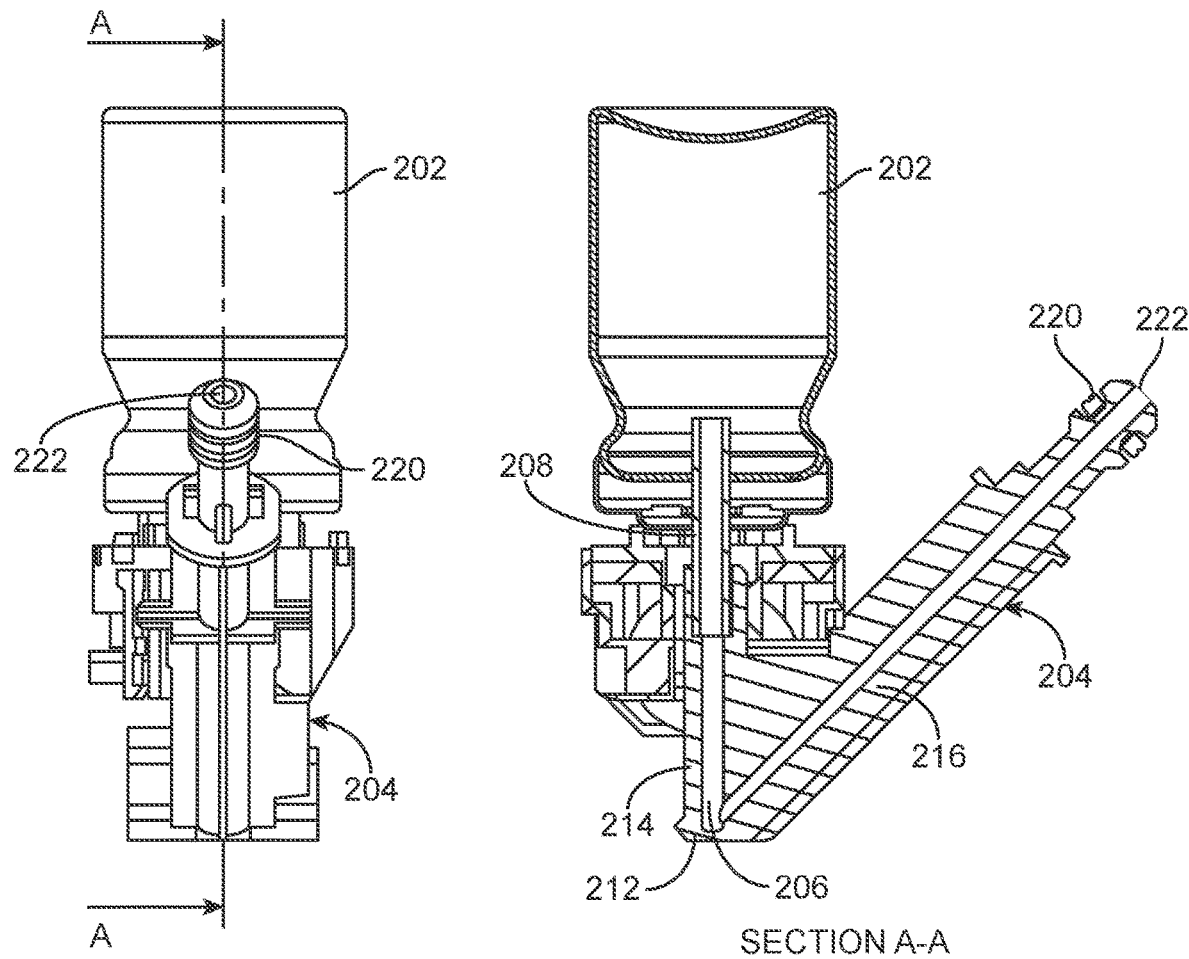
FIGS. 3A and 3B illustrate a side view and a cross-sectional view, respectively, of an internal assembly housed within the device of FIGS. 1A and 1B, in accordance with one or more embodiments.

FIGS. 3A and 3B illustrate a side view and a cross-sectional view, respectively, of the internal assembly housed within the device of FIGS. 1A and 1B, in accordance with one or more embodiments. As previously described, the internal assembly comprises the propellant canister 202 and the junction 204 having the propellant channel 206. FIGS. 3A and 3B also show the metering valve 208 and the sealing ring 220.

Figure 4A:
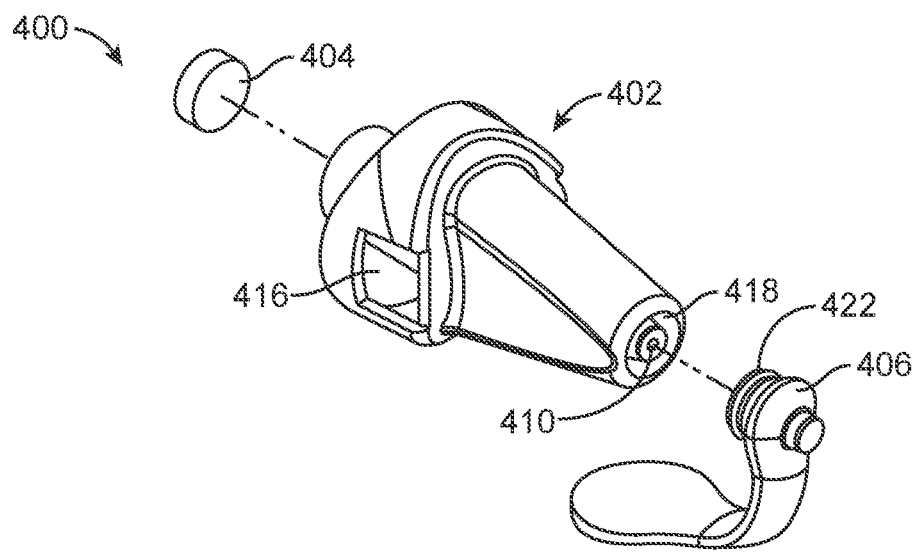
FIGS. 4A and 4B illustrate an exploded view and a cross-sectional view, respectively, of a nozzle, in accordance with one or more embodiments.
Figure 4B:
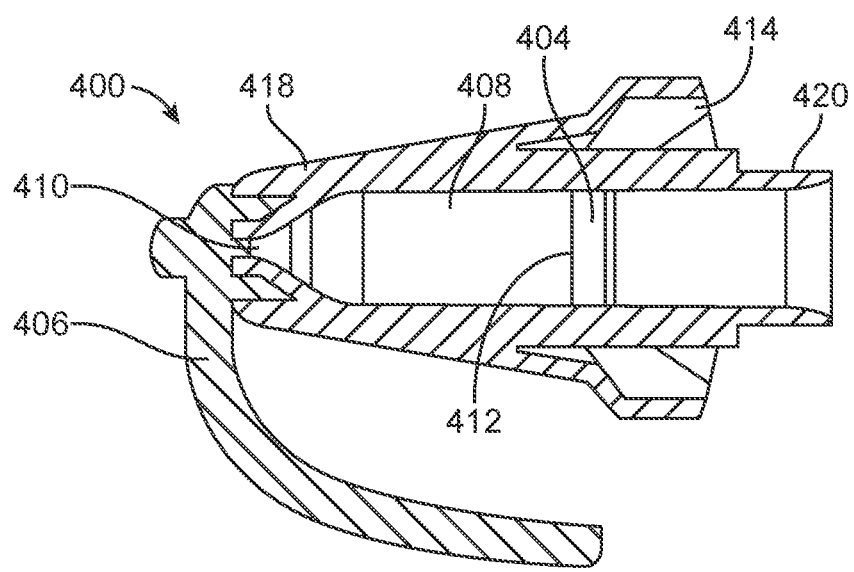

FIGS. 4A and 4B illustrate an exploded view and a cross-sectional view, respectively, of a nozzle 400, in accordance with one or more embodiments. The nozzle 400 is an embodiment of the nozzle 104. In the embodiment of FIGS. 4A and 4B, the nozzle 400 comprises a nozzle body 402, a diffuser 404, and a removable seal 406. The removable seal 406 is a seal that retains the drug compound within the nozzle 400 and may be removed by a user before delivery of the dose. The nozzle body 402 comprises a nozzle channel 408, an outlet orifice 410, a ledge 412, a reciprocal mating interface 414 (for coupling the housing body 102), an opening 416 (for receiving the securing latch 118), a tip seal interface 418, and an ejector sleeve interface 420. For the sake of clarity, the description of corresponding elements in FIGS. 1-3 is incorporated herein for FIGS. 4A and 4B.

In the embodiments of FIGS. 4A and 4B, a diameter of the nozzle channel 408 tapers toward the outlet orifice 410. This configuration may beneficially increase the velocity of the drug compound before it exits the outlet orifice 410. In addition, this configuration may beneficially decrease the plume width, enabling the drug compound to be propelled further into the nasal cavity and into the upper regions of the nasal cavity (e.g., the middle and superior turbinate regions and/or the olfactory region). In alternate embodiments, the nozzle channel 408 may be cylindrical or conical in shape. The design of the nozzle 400 may optimized for various compounds having different characteristics. For example, the diameter of the nozzle channel, the angle and/or shape of the taper, the diameter of the outlet orifice may be modified (e.g., increased or decreased) to suitably deliver the compound to the upper nasal cavity. As an example, larger nozzles may be used for some drug compounds in powder form to prevent clogging within the nozzle.

The ledge 412 is a surface within the nozzle channel 408 against which the diffuser 404 is seated. In the embodiments of FIGS. 4A and 4B, a proximal portion of the nozzle channel 408 (closer to the propellant channel 206) has a greater diameter than a distal portion of the nozzle channel 408 (closer to the outlet orifice 410), thereby creating the ledge 412 between the two portions. In one embodiment, the proximal portion comprises a tapered or chamfered portion that leads to ledge 412 to facilitate the placement of the diffuser 404 within the nozzle channel 408.

The tip seal interface 418 is positioned at a tip of the nozzle 400 and couples to the removable seal 406. In the embodiments of FIGS. 4A and 4B, the tip seal interface 418 is a cavity surrounding the outlet orifice 410 that receives a reciprocal securing interface 422 of the removable seal 406. The removable seal 406 is in the shape of a pull tab but may have other suitable geometries for sealing the outlet orifice 410 and providing a portion that a user may grab to remove the removable seal 406 from the nozzle body 402. In this configuration, the removable seal 406 retains the drug compound within the nozzle channel 408 and prevents the drug compound from prematurely coming out of the outlet orifice 410. The removable seal 406 also maintains the integrity of the drug compound (i.e., preventing contamination) until the dose is to be delivered. In one embodiment, a portion of the removable seal 406 inserts into the outlet orifice 410. Accordingly, the drug compound is secured within the nozzle channel 408 between the diffuser 404 and the removable seal 406. The removable seal 406 may be removed (e.g., by twisting, pulling, tearing, or similar) from the tip seal interface 418 once the dose is ready to be delivered to a user's upper nasal cavity.

Figure 6A:
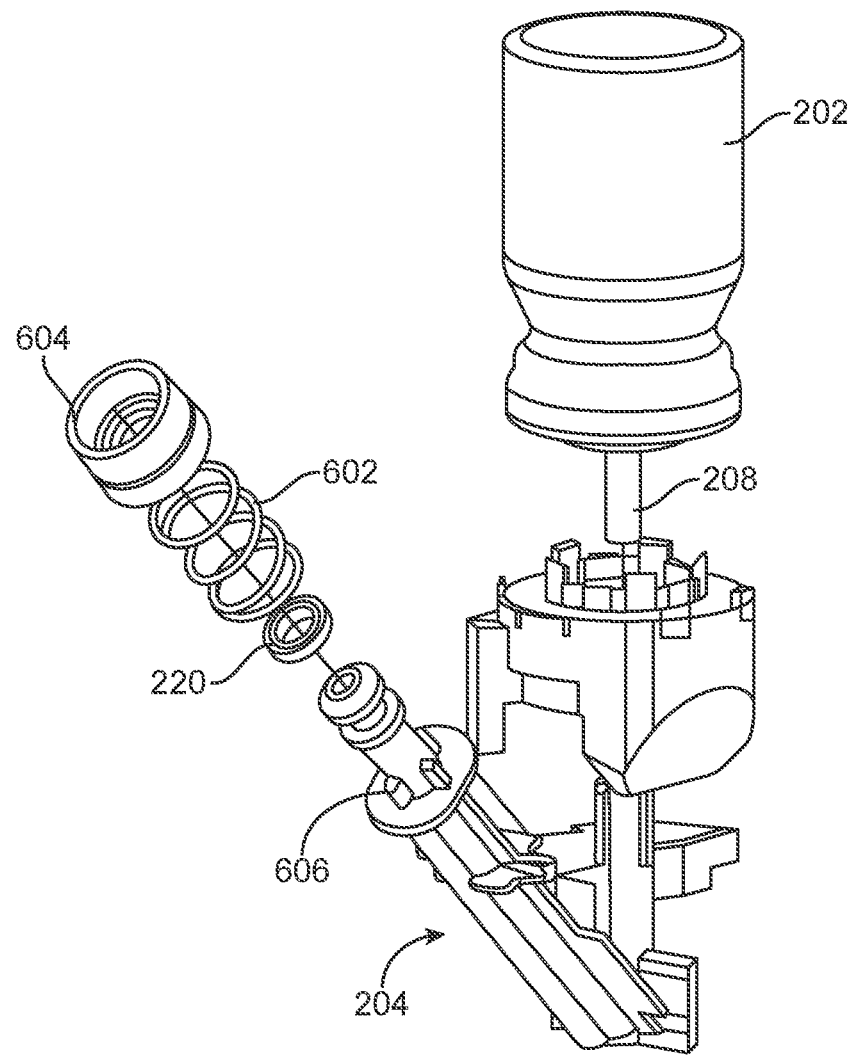
FIGS. 6A and 6B illustrate an exploded view of the internal assembly and the internal assembly seated within a housing body, respectively, in accordance with one or more embodiments.
Figure 6B:
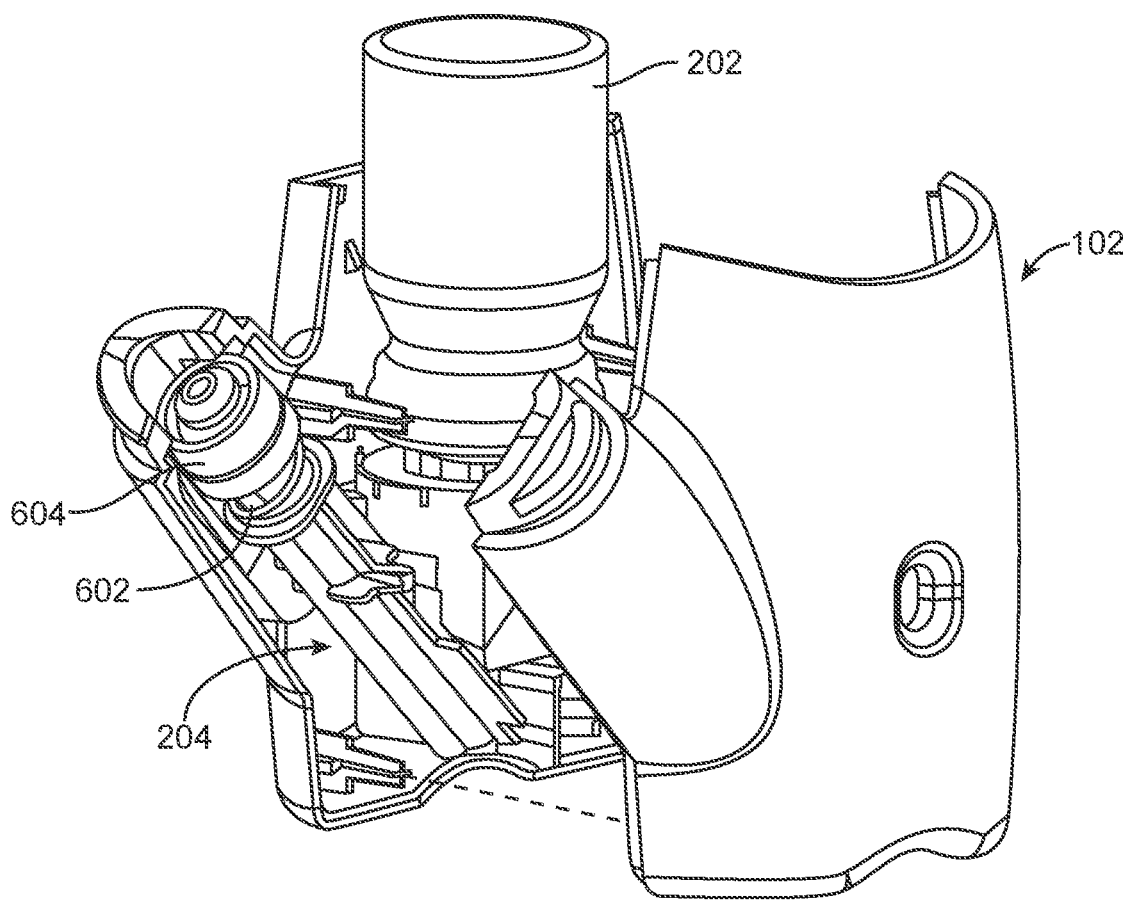

The ejector sleeve interface 420 is configured to couple to an ejector sleeve, which is described in further detail in FIGS. 6A and 6B. The ejector sleeve is a component of the coupling mechanism that enables the nozzle 400 to decouple from the housing body 102. In the embodiments of FIGS. 4A and 4B, the ejector sleeve interface 420 is a ledge about an external surface of the nozzle channel 408. The ejector sleeve is a ring-like structure (shown in FIG. 6A) that slides onto and mates with the ejector sleeve interface 420.

Figure 5A:
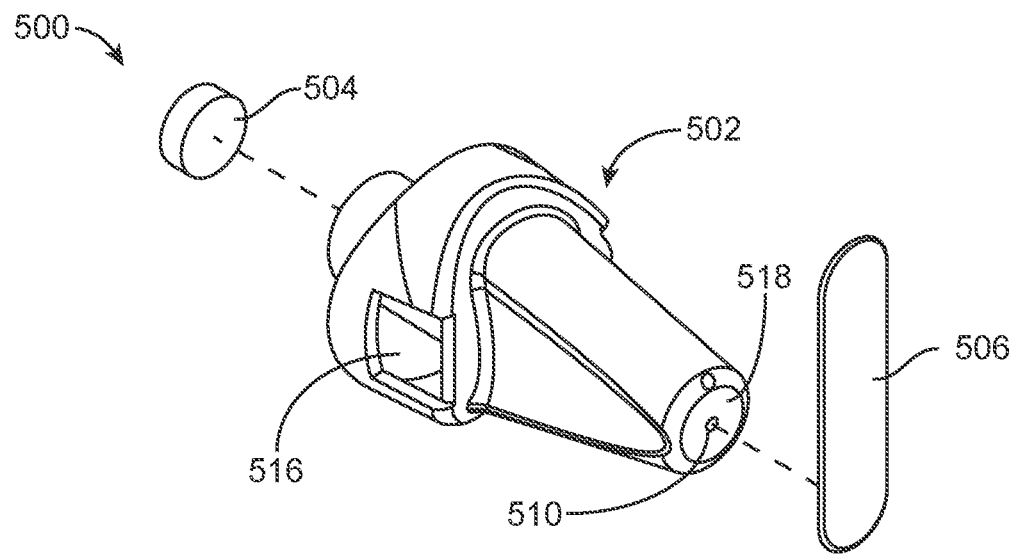
FIGS. 5A and 5B illustrate an exploded view and a cross-sectional view, respectively, of a nozzle, in accordance with one or more embodiments.
Figure 5B:
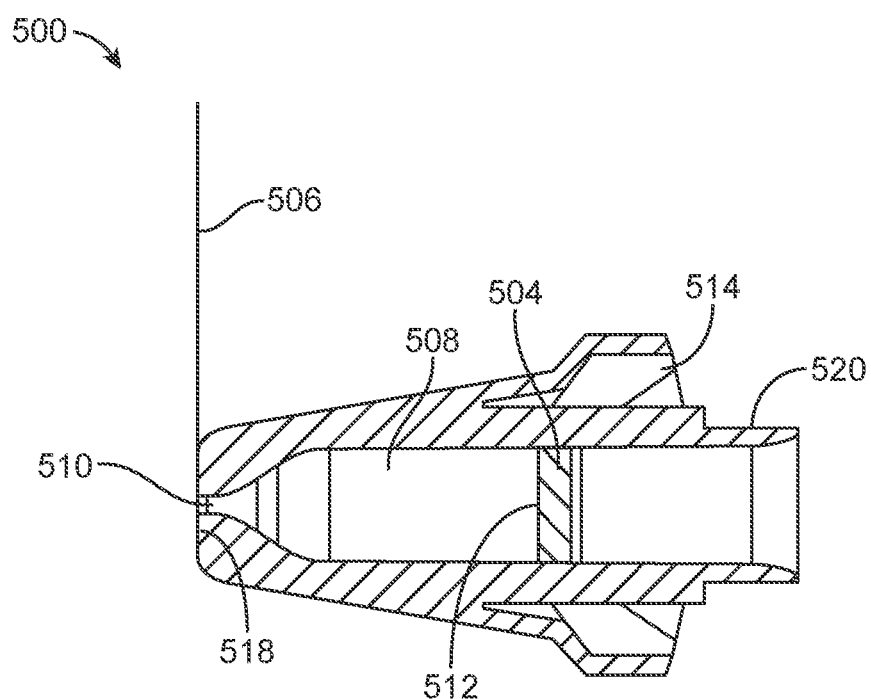

FIGS. 5A and 5B illustrate an exploded view and a cross-sectional view, respectively, of a nozzle, in accordance with one or more embodiments. The nozzle 500 is an embodiment of the nozzle 104 or the nozzle 400. In the embodiment of FIGS. 5A and 5B, the nozzle 500 comprises a nozzle body 502, a diffuser 504, and a removable seal 506. The nozzle body 502 comprises a nozzle channel 508, an outlet orifice 510, a ledge 512, a reciprocal mating interface 514 (for coupling the housing body 102), an opening 516 (for receiving the securing latch 118), a tip seal interface 518, and an ejector sleeve interface 520. For the sake of clarity, the description of corresponding elements in FIGS. 1-4 is incorporated herein for FIGS. 5A and 5B.

In the embodiments of FIGS. 5A and 5B, the removable seal 506 is in the shape of a foil tab that may be adhered to the tip seal interface 518, which is a surface surrounding the outlet orifice 510. In other embodiments, the removable seal 506 may have other suitable geometries for sealing the outlet orifice 410 and providing a portion that a user may grab to remove the removable seal 406 from the nozzle body 402.

FIGS. 6A and 6B illustrate an exploded view of the internal assembly and the internal assembly seated within a portion of the housing body 102, respectively, in accordance with one or more embodiments. In FIG. 6A, additional components of the coupling mechanism for coupling and decoupling the nozzle 104 to and from the housing body 102 are shown. In the embodiment of FIGS. 6A and 6B, the coupling mechanism enables the nozzle 104 to be positioned on and secured to a distal end of the stem 112 and enables the nozzle 104 to be released from the stem 112 upon depression of the release button 116. In particular, the coupling mechanism retains the nozzle 104 on the distal end of the stem 112 after the nozzle 104 is released to prevent the nozzle 104 from fully ejecting off the stem 112. These components comprise a compression spring 602 and an ejector sleeve 604.

The compression spring 602 is positioned about a distal end of the second branch of the junction. In the embodiments of FIGS. 6A and 6B, a first end of the compression spring 602 is coupled to the second branch via one or more engagement ribs 606, and a second end of the compression spring 602 is coupled to the ejector sleeve 604. In FIG. 6A, the compression spring 602 is shown at its full length (at rest). The compression spring 602 may be compressed when a force is applied to it.

The ejector sleeve 604 couples to an ejector sleeve interface of a nozzle (as described in FIGS. 4A and 4B). In the embodiment of FIGS. 6A and 6B, the ejector sleeve 604 is a ring-like structure that mates with the ejector sleeve interface of the nozzle. A proximal end of the ejector sleeve 604 is coupled to the compression spring 602 such that the ejector sleeve 604 moves with the compression spring 602 as the compression spring 602 is fully compressed, partially compressed, or returning to a resting length. FIG. 6B illustrates the internal assembly seated within a portion of the housing body 102, where the compression spring 602 is partially compressed such that the ejector sleeve 604 may be positioned within the housing body 102. In some embodiments, the compression spring 602 may be at rest when positioned within the housing body 102.

When a nozzle is coupled to the housing body 102, the nozzle couples to the ejector sleeve 604 and compresses the compression spring 602 such that the securing latch of the release button mates with the opening on the nozzle. In this configuration, the ejector sleeve 604 moves between a first position, in which the compression spring 602 is partially compressed, and a second position, in which the compression spring 602 is further partially compressed or fully compressed. In one embodiment, the ejector sleeve 604 moves between a first position, in which the compression spring 602 is at rest, and a second position, in which the compression spring 602 is partially compressed or fully compressed. The ejector sleeve 604 transitions between the first position and the second position as the nozzle is being coupled to the housing body 102 or as the nozzle is being decoupled from the housing body 102.

As previously described, to decouple the nozzle from the housing body 102, a user provides user input to the release button 116, which displaces the securing latch from the opening in the nozzle. Once the securing latch is displaced from the nozzle opening, the ejector sleeve 604 transitions from the second position to the first position. In the embodiment of FIGS. 6A and 6B, a protrusion (e.g., in the shape of a wedge or ramp) on an internal surface of a first side of the housing body 102 contacts the ejector sleeve 604 and biases the movement of the ejector sleeve 604 towards a second side of the housing body 102. Thus, as the ejector sleeve 604 transitions from the second position to the first position, the nozzle coupled to the ejector sleeve 604 abuts the second side of the housing body 102. In this configuration, friction created between the nozzle and the side of the housing body 102 prevents the nozzle from fully ejecting from the housing body 102 (i.e., launching off of the housing body 102) such that the nozzle remains on a distal portion of the stem 112 once decoupled from the housing body 102, enabling a user to manually remove the decoupled nozzle from the stem 112.

Figure 7A:
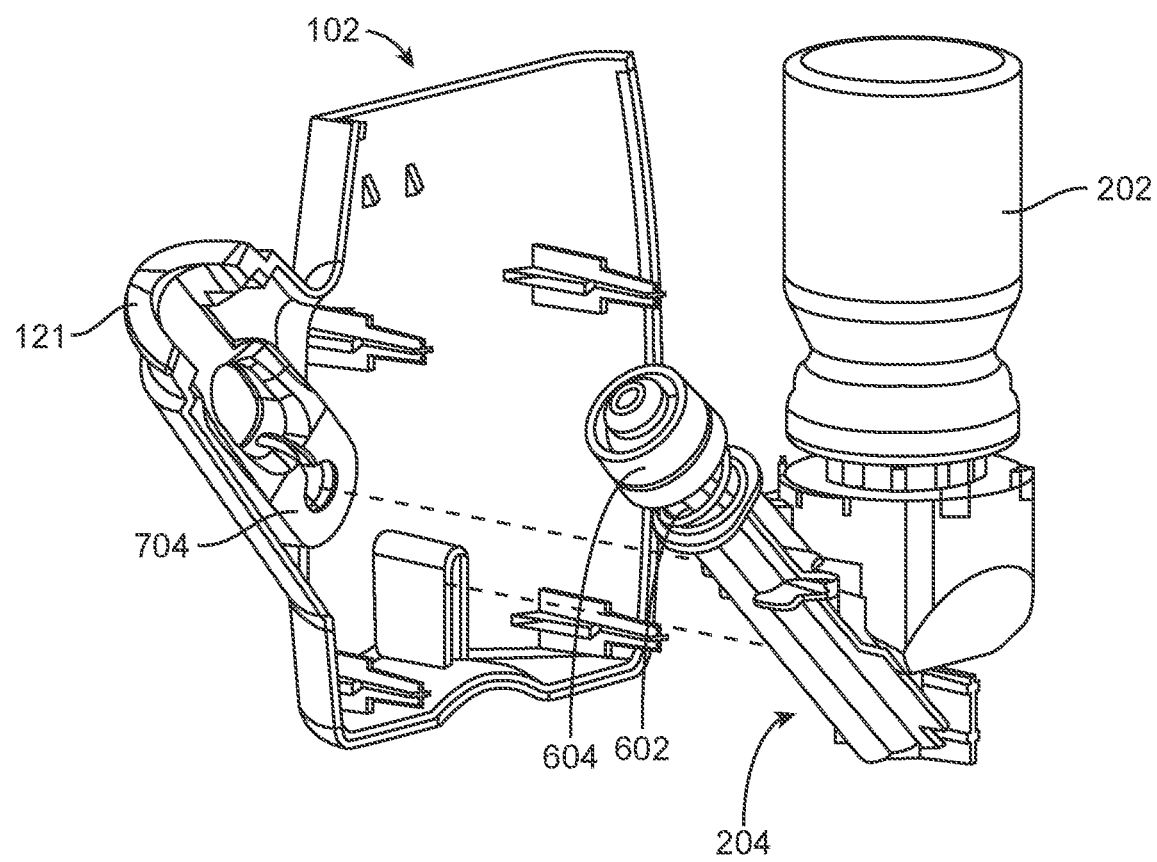
FIGS. 7A-7C illustrate an internal surface of the housing of the device of FIGS. 1A and 1B and a release button, in accordance with one or more embodiments.
Figure 7B:
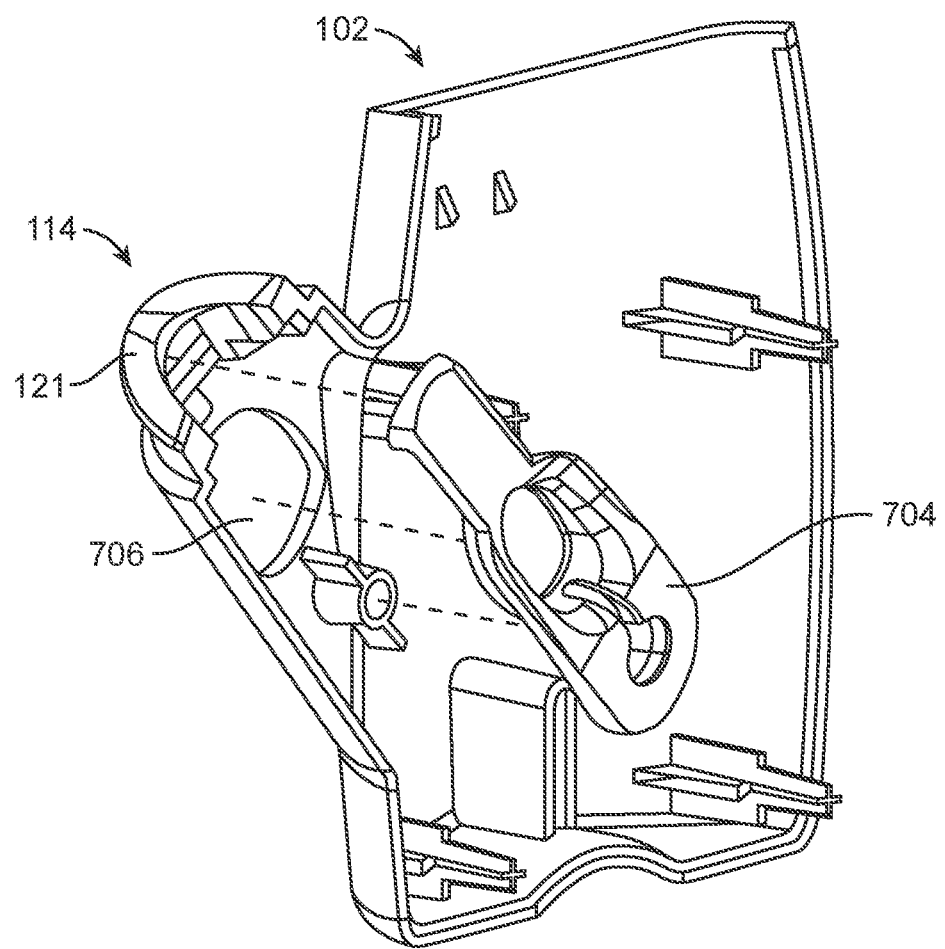
Figure 7C:
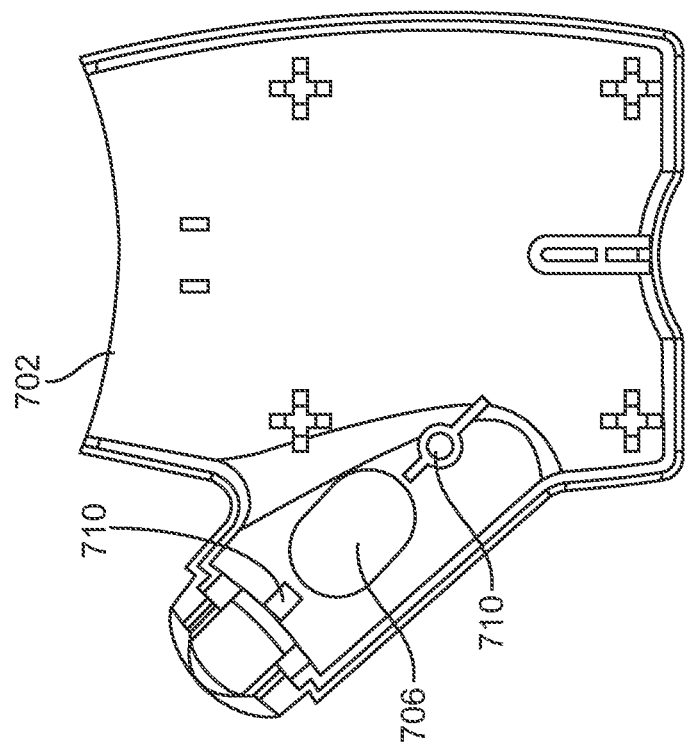
Figure 7C:
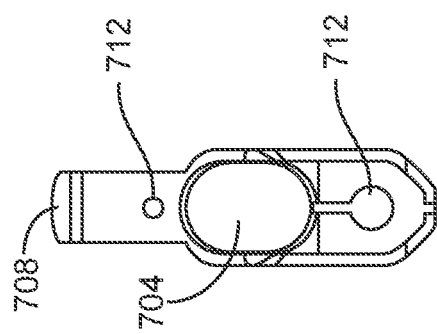

FIGS. 7A-7C illustrate an internal surface 702 of the housing body 102 and a release button 704, in accordance with one or more embodiments. In the embodiments of FIGS. 7A-7C, the release button 704 is coupled to the internal surface 702, specifically an internal surface of the stem 112 which comprises an opening 706 for exposing the release button 704. The release button 704 is positioned such that a securing latch 708 directly connected to the release button 704 protrudes through the opening 706 in the mating interface 114. The release button 704 may have one or more locating features 710 that mate with reciprocal locating features 712 on the internal surface 702 for fine tune alignment of the release button 704. In one embodiment, the release button 704 is molded with a bend such that, when the device is assembled and the junction 204 is positioned against the release button 704, the securing latch is pre-loaded to better retain the nozzle.

Figure 8:
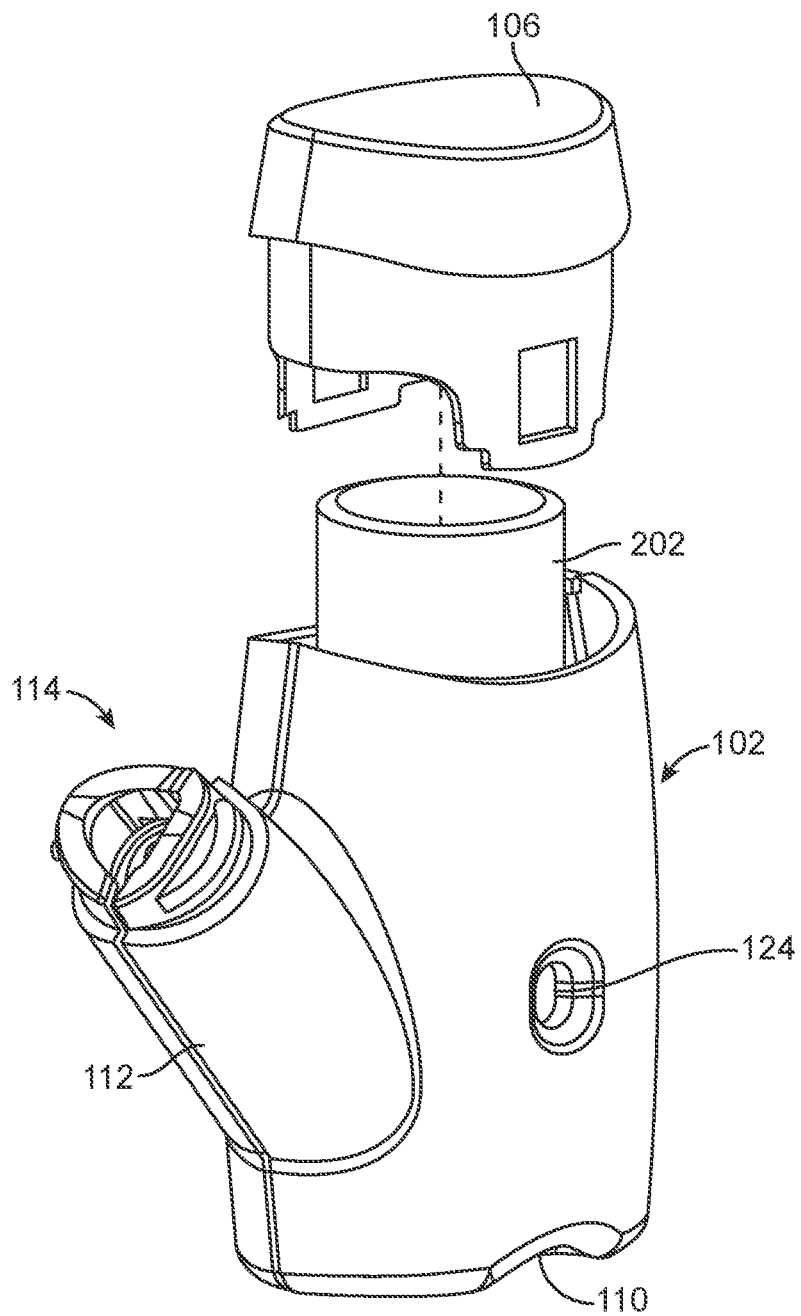
FIG. 8 a perspective, partially exploded view of the device of FIGS. 1A and 1B, in accordance with one or more embodiments.

FIG. 8 a perspective, partially exploded view of the device of FIGS. 1A and 1B, in accordance with one or more embodiments. FIG. 8 illustrates the housing body 102 with the actuator 106 removed and without a nozzle. In some embodiments, the propellant canister 202 may be replaced such that the device 100 may be reused.

ADDITIONAL CONFIGURATION INFORMATION

The foregoing description of the embodiments of the disclosure has been presented for the purpose of illustration; it is not intended to be exhaustive or to limit the disclosure to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based hereon. Accordingly, the disclosure of the embodiments is intended to be illustrative, but not limiting, of the scope of the disclosure, which is set forth in the following claims.

What is claimed is:

1. A device for delivering a compound to an upper nasal cavity comprising:
    a housing body;
    an actuator configured to move relative to the housing body, wherein actuation of the actuator is configured to actuate a canister thereby releasing a contained propellant;
    a stem protruding from the housing body, the stem comprising a delivery opening at a distal end of the stem and a mating interface positioned about the delivery opening, the mating interface comprising an opening, wherein the mating interface is configured to mate with a nozzle containing the compound;
    a release button positioned within the housing body and configured to move relative to the housing body, the release button directly connected to a securing latch that is configured to protrude radially outwardly through the opening of the mating interface, wherein the securing latch is configured to mate with a reciprocal securing interface on the nozzle, thereby coupling the nozzle to the mating interface, and wherein actuation of the release button is configured to displace the securing latch from the reciprocal securing interface, thereby decoupling the nozzle from the mating interface;
    a junction positioned within the housing body, the junction comprising:
        a base;
        a first branch of the junction extending from the base, the first branch comprising a propellant channel configured to be in fluid communication with the canister; and
        a second branch of the junction extending from the base, the second branch in fluid communication with the first branch; and
    a coupling mechanism configured to removably couple and decouple the nozzle to the stem, the coupling mechanism comprising:
        a compression spring positioned about a distal end of the second branch;
        an ejector sleeve coupled to a distal end of the compression spring, the ejector sleeve configured to couple to a portion of the nozzle, wherein the ejector sleeve is configured to translate between a first position, in which the compression spring is at rest, and a second position, in which the compression spring is compressed; and
        wherein when the nozzle is coupled to the stem, the ejector sleeve is configured to be in the second position, and wherein when the release button is depressed, the securing latch is configured to release the nozzle, thereby enabling the ejector sleeve to return to the first position and decoupling the nozzle from the stem.

2. The device of claim 1, wherein as the ejector sleeve returns to the first position, a portion of the ejector sleeve is configured to slide along an internal surface of the housing body, thereby impeding the movement of the ejector sleeve.

3. The device of claim 1, wherein the actuator is positioned at a top portion of the housing body.

4. The device of claim 1, wherein the actuator is configured to translate relative to the housing body.

5. The device of claim 1, wherein the housing body further comprises a dose counter that is configured to count a number of actuations of the canister.

6. The device of claim 1, further comprising a sealing mechanism configured to create a seal between the stem and the nozzle coupled to the stem.

7. The device of claim 6, wherein the sealing mechanism is an x-ring positioned about a distal end of the stem.

8. The device of claim 1, further comprising the canister.

9. The device of claim 1, further comprising the nozzle containing the compound.

10. The device of claim 9, wherein the nozzle comprises a compound channel and an outlet orifice disposed at a distal end of the compound channel, wherein the compound channel is configured to be in fluid communication with the propellant channel when the nozzle is coupled to the stem such that the released propellant travels through the propellant channel into the compound channel and propels the compound out the outlet orifice.

11. The device of claim 1, wherein the housing body comprises a first clamshell and a second clamshell that are configured to couple together.

12. A device for delivering a compound to an upper nasal cavity comprising:
   a housing body;
   an actuator configured to move relative to the housing body, wherein actuation of the actuator is configured to actuate a canister thereby releasing a contained propellant;
   a stem protruding from the housing body, the stem comprising a mating interface that is configured to mate with a nozzle containing the compound;
   a release button positioned within the housing body and configured to move relative to the housing body, the release button directly connected to a securing mechanism that is configured to couple the nozzle to the mating interface, and wherein actuation of the release button is configured to decouple the nozzle from the mating interface, wherein the mating interface comprises an opening, and the securing mechanism comprises a securing latch that is configured to protrude radially outwardly through the opening of the mating interface; and
   a coupling mechanism configured to removably couple and decouple the nozzle to the stem when the release button is depressed, thereby decoupling the nozzle from the stem, the coupling mechanical comprising:
      a compression spring positioned near a distal end of the stem; and
      an ejector sleeve coupled to a distal end of the compression spring, the ejector sleeve configured to couple to a portion of the nozzle when the nozzle is coupled to the stem, wherein the ejector sleeve is configured to move between a first position, in which the compression spring is at rest, and a second position, in which the compression spring is compressed.

13. The device of claim 12, wherein coupling the nozzle to the mating interface comprises the securing latch mating with a reciprocal securing interface on the nozzle, and decoupling the nozzle from the mating interface comprises the release button displacing the securing latch from the reciprocal securing interface on the nozzle.

14. The device of claim 12, further comprising:
   a junction positioned within the housing body, the junction comprising a propellant channel configured to be in fluid communication with the canister.

15. The device of claim 12, wherein when the nozzle is coupled to the stem, the ejector sleeve is configured to be in the second position, and wherein when the release button is depressed, the securing latch is configured to release the nozzle, thereby enabling the ejector sleeve to return to the first position and decoupling the nozzle from the stem.

16. The device of claim 12, wherein as the ejector sleeve returns to the first position, a portion of the ejector sleeve is configured to slide along an internal surface of the housing body, thereby impeding the movement of the ejector sleeve.

17. The device of claim 12, wherein the actuator is positioned at a top portion of the housing body.

18. The device of claim 12, wherein the actuator is configured to translate relative to the housing body.

19. The device of claim 12, wherein the housing body further comprises a dose counter that is configured to count a number of actuations of the canister.

20. The device of claim 12, further comprising a sealing mechanism configured to create a seal between the stem and the nozzle coupled to the stem.

21. The device of claim 20, wherein the sealing mechanism is an x-ring positioned about a distal end of the stem.

22. The device of claim 12, further comprising the canister.

23. The device of claim 12, further comprising the nozzle containing the compound.

24. The device of claim 23, wherein the nozzle comprises a compound channel and an outlet orifice disposed at a distal end of the compound channel, wherein the compound channel is configured to be in fluid communication with the propellant channel when the nozzle is coupled to the stem such that the released propellant travels through the propellant channel into the compound channel and propels the compound out the outlet orifice.

25. The device of claim 12, wherein the housing body comprises a first clamshell and a second clamshell that are configured to couple together.

* * * * *